US008809623B2

(12) United States Patent
Milach et al.

(10) Patent No.: US 8,809,623 B2
(45) Date of Patent: Aug. 19, 2014

(54) GENETIC LOCI ASSOCIATED WITH RESISTANCE TO TROPICAL RUST IN MAIZE

(75) Inventors: Sandra Cristina Kothe Milach, Passo Fundo (BR); Victor Llaca, Newark, DE (US); Marymar Goncalves Butruille, Des Moines, IA (US); Emerson Limberger, Montenegro (BR); Elcio De Oliveira Alves, Itumbiara (BR)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 283 days.

(21) Appl. No.: 12/939,226

(22) Filed: Nov. 4, 2010

(65) Prior Publication Data

US 2011/0107453 A1 May 5, 2011

Related U.S. Application Data

(60) Provisional application No. 61/257,977, filed on Nov. 4, 2009.

(51) Int. Cl.

| | |
|---|---|
| ***A01H 5/00*** | (2006.01) |
| ***A01H 1/00*** | (2006.01) |
| ***A01H 1/02*** | (2006.01) |
| ***C12N 15/00*** | (2006.01) |
| ***C12Q 1/68*** | (2006.01) |

(52) U.S. Cl.
USPC ........ 800/267; 800/265; 800/279; 800/320.1; 435/6.1

(58) Field of Classification Search
USPC ................. 800/265, 267, 279, 320.1; 435/6.1
See application file for complete search history.

(56) References Cited

U.S. PATENT DOCUMENTS

2006/0141495 A1 6/2006 Wu

OTHER PUBLICATIONS

Lima et al. Maydica 45(2): 105-108, 2000, Abstract.*
Chavez-Medina, J.A. and Leyva-Lopez, N.E. 2007. Resistance to *Puccinia polysora* in maize accessions. Plant Dis. 91:1489-1495.
Chen et al. 2004. Molecular tagging and genetic mapping of the disease resistance gene RPPQ to southern corn rust. Theor Appl Genet 108:945-950.
Collins, N. et al. 1999. Molecular characterization of the maize Rp1-D rust resistance haplotype and its mutants. The Plant Cell 11:1365-1376.
Holland, J.B. et al. 1998. Inheritance of resistance to southern corn rust in tropical-by-corn-belt maize populations. Theor Appl Genet 96:232-241.
Hu, G. et al. 1996. Disease lesion mimicry caused by mutations in the rust resistance gene rp1. The Plant Cell 8:1367-1376.
Hyten, D.L. et al 2009 Bulked segregant analysis using the GoldenGate Assay to Locate the Rpp3 locus that confers resistance to soybean rust in soybean. Crop Science 49:267-271.
Jines, M.P. et al. 2007. Mapping resistance to Southern rust in a tropical by temperatre maize recombinant inbred topcross population. Theor Appl Genet 114:695-667.
Kerns, M.R. et al. 1999. QTL for resistance to common rust and smut in maize. Maydica 44:37-45.
Kraja, A. et al. 2000. Identification of tropical and temperate maize populations having favorable alleles for disease resistance. Crop Sci 40:948-954.
Lima, M. et al. 2000. Inheritance of the resistance to tropical rust caused by *Physopella zeae* in maize. Maydica 45:105-108.
Lubberstedt, T. et al. 1998. Comparative quantitative trait loci mapping of partial resistance to *Puccinia sorghi* across four populations of European flint maize. Phytopathology. 88:1324-1329.
Makumbi et al. Combining Ability and Heterosis in Tropical Maize Inbreds under Stress and Optimal Conditions. The ASA-CSSA-SSSA International Annual Meetings (Nov. 6-10, 2005), Salt Lake City, UT.2005.
Moon, H.G. et al. 1999. Major QTLs for disease resistance and other traits identified in recombinant inbred lines from tropical maize hybrids. Maydica 44:301-311.
Sudupak, M.A. et al. 1993. Unequal exchange and meiotic instability of disease-resistance genes in the Rp1 region of maize. Genetics 133:119-125.
Wisser, R.J. et al. 2005. The genetic architecture of disease resistance in maize: a synthesis of published studies. Phytopathology 96:120-129.
Zhou, C. 2007. Characterization and fine mapping of RppQ, a resistance gene to southern corn rust in maize. Mol Genet Genomics 278:723-728.
de Souza, S. G. H et al., Comparative analysis of Genetic Diversity Among the Maize Inbred lines (*Zea mays* L.) Obtained by RAPD and SSR Markers, Braz. arch. biol. technol., Jan.-Feb. 2008, pp. 183-192, vol. 51, N. 1.
Lima, Marlene et al., Tropical rust evaluation in maize inbred lines, Bragantia, 1996, pp. 269-273, vol. 55, N. 2 (Abstract only).
Zhang, Ya et al., Mapping of southern corn rust-resistant genes in the W2D inbred line of maize (*Zea mays* L.), Mol. Breeding, 2010, pp. 433-439, vol. 25.
Wilson, R. K., Maize genome, Sep. 23, 2013, EMBL Accession No. AC195216.

* cited by examiner

*Primary Examiner* — Medina A Ibrahim

(57) ABSTRACT

The invention relates to methods and compositions for identifying maize plants that have increased or decreased resistance to tropical rust. The methods use molecular markers to identify and select plants with increased resistance to tropical rust or to identify and counter-select plants with decreased resistance to tropical rust. Maize plants generated by the methods of the invention are also a feature of the invention. Also of interest are methods used to correlate allelic variation with a trait of interest.

5 Claims, 8 Drawing Sheets

PH468 x PHS6Y F2 POPULATION DISTRIBUTION
A
Frequency
0
20
40
60
80
100
120
140
1
2
3
4
5
6
7
8
9
TRPRST Score
PH468
PHS6Y
B
Frequency
0
10
20
30
40
50
60
70
80
90
2
3
4
5
6
7
8
9
SOURST Score
PH468
PHS6Y

FIG. 5

HYBRID GEID6170295

TRPRST
Resistant

TRPRST
Susceptible

FIG. 7

| Start | Sequence (positions 520, 530, 540 marked on reference) | SEQ ID NO: | Group |
|---|---|---|---|
| | G T T G A T G A G T T T T T T T T A G T T A G C T C C X A A | | |
| 506 | G T T G A T G A G T T T T T T T - A G T T A G C T C C A A A | 137 | R |
| 506 | G T T G A T G A G T T T T T T T - A G T T A G C T C C N A A | 138 | R |
| 505 | G T T G A T G A G T T T T T T T - A G T T A G C T C C A A A | 139 | R |
| 507 | G T T G A T G A G T T T T T T T - A G T T A G C T C C N A A | 140 | R |
| 506 | G T T G A T G A G T T T T T T T - A G T T A G C T C C N A A | 141 | R |
| 506 | G T T G A T G A G T T T T T T T - A G T T A G C T C C A A A | 142 | R |
| 504 | G T T G A T G A G T T T T T T T T A G T T A G C T C C A A A | 143 | S |
| 505 | G T T G A T G A G T T T T T T T T A G T T A G C T C C A A A | 144 | S |
| 510 | G T T G A T G A G T T T T T T T T A G T T A G C T C C A A A | 145 | S |
| 507 | G T T G A T G A G T T T T T T T T A G T T A G C T C C N A A | 146 | S |
| 504 | G T T G A T G A G T T T T T T T T A G T T A G C T C C N A A | 147 | S |
| 505 | G T T G A T G A G T T T T T T T T A G T T A G C T C C N A A | 148 | S |
| 503 | G T T G A T G A G T T T T T T T T A G T T A G C T C C N A A | 149 | S |
| 508 | G T T G A T G A G T T T T T T T T A G T T A G C T C C N A A | 150 | S |
| 506 | G T T G A T G A G T T T T T T T T A G T T A G C T C C N A A | 151 | S |
| 509 | G T T G A T G A G T T T T T T T T A G T T A G C T C C A A A | 152 | S |
| 505 | N T T G A T G A G T T T T T T T T A G T A A N C T C C N A A | 153 | S |
| 508 | G T T G A T G A G T T T T T T T T A G T T A G C T C C N A A | 154 | S |

PHMTR region (SEQ ID NO: 155)

FIG. 8

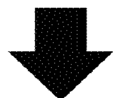

```
T G A A C T T A A C C T X X X A A G A A A T G A C A C A C A

T G A A C T T A A C C T G A G A A G A A A T G A C A C A C A   PHS6Y
T G A A C T T A A C C T G A G A A G A A A T G A C A C A C A   PH1FT71
T G A A C T T A A C C T G A G A A G A A A T G A C A C A C A   PH1JG22
T G A A C T T A A C C T G A G A A G A A A T G A C A C A C A   PH1G3H1
T G A A C T T A A C C T G A G A A G A A A T G A C A C A C A   PH1JG01
T G A A C T T A A C C T G C G A A G A A A T G A C A C A C G   PH147G5
T G A A C T T A A C C T G C G A A G A A A T G A C A C A C G   PHP3P1
T G A A C T T A A C C T G C G A A G A A A T G A C A C A C G   PH1AGK1
T G A A C T T A A C C T G C G A A G A A A T G A C A C A C A   PHBNA
T G A A C T T A A C C T G C G A A G A A A T G A C A C A C A   Mo17
T G A A C T T A A C C T G C G A A G A A A T G A C A C A C A   PHY7M2
T G A A C T T A A C C T G C G A A G A A A T G A C A C A C A   PH467
T G A A C T T A A C C T A C G A A G A A A T G A C A C A C A   PH9PR
T G A A C T T A A C C T A C G A A G A A A T G A C A C A C A   PH7WC
T G A A C T T A A C C T A C G A A G A A A T G A C A C A C A   PH48F
T G A A C T T A A C C T A C G A A G A A A T G A C A C A C A   PHDGA
T G A A C T T A A C C T A C G A A G A A A T G A C A C A C A   B73-1
T G A A C T T A A C C T A C G A A G A A A T G A C A C A C A   PH0TJ
T G A A C T T A A C C T A C G A A G A A A T G A C A C A C A   B73
T G A A C T T A A C C T A C A A A G A A A T G A C A C A C A   PH9VF
T G A A C T T A A C C T A C G A A G A A A T G A C A C A C A   PH7W3
```

R (PHS6Y, PH1FT71, PH1JG22, PH1G3H1, PH1JG01)

S (PH147G5 through PH7W3)

R = resistant to tropical and southern rust

S = susceptible to tropical and southern rust

SEQUENCE LISTING

<160> NUMBER OF SEQ ID NOS: 167

<210> SEQ ID NO 1
<211> LENGTH: 33
<212> TYPE: DNA
<213> ORGANISM: Artificial sequence
<220> FEATURE:
<223> OTHER INFORMATION: PHM1192-26-U FW primer

<400> SEQUENCE: 1
agttttgggt tttctwttgr aaggtggaag cca 33

<210> SEQ ID NO 2
<211> LENGTH: 22
<212> TYPE: DNA
<213> ORGANISM: Artificial sequence
<220> FEATURE:
<223> OTHER INFORMATION: PHM1192-26-U RV primer

<400> SEQUENCE: 2
acagactaac cgtgcccctt gt 22

<210> SEQ ID NO 3
<211> LENGTH: 25
<212> TYPE: DNA
<213> ORGANISM: Artificial sequence
<220> FEATURE:
<223> OTHER INFORMATION: PHM1192-26-U Probe-1

<400> SEQUENCE: 3
cgcgccgagg gcagctgagg agagt 25

<210> SEQ ID NO 4
<211> LENGTH: 28
<212> TYPE: DNA
<213> ORGANISM: Artificial sequence
<220> FEATURE:
<223> OTHER INFORMATION: PHM1192-26-U Probe-2

<400> SEQUENCE: 4
acggacgcgg agacagctga ggagagtg 28

<210> SEQ ID NO 5
<211> LENGTH: 35
<212> TYPE: DNA
<213> ORGANISM: Artificial sequence
<220> FEATURE:
<223> OTHER INFORMATION: PHM1192-4 FW primer

<400> SEQUENCE: 5
tcgaggagca ggtataaaat aaaatgctwc caaca 35

<210> SEQ ID NO 6
<211> LENGTH: 29
<212> TYPE: DNA
<213> ORGANISM: Artificial sequence
<220> FEATURE:
<223> OTHER INFORMATION: PHM1192-4 RV primer

<400> SEQUENCE: 6
cttggagacc ttatttatgg cttccacct 29

<210> SEQ ID NO 7
<211> LENGTH: 28
<212> TYPE: DNA
<213> ORGANISM: Artificial sequence
<220> FEATURE:
<223> OTHER INFORMATION: PHM1192-4 Probe-1

<400> SEQUENCE: 7
cgcgccgagg cagaattccg tcgtgtaa 28

<210> SEQ ID NO 8
<211> LENGTH: 30
<212> TYPE: DNA
<213> ORGANISM: Artificial sequence
<220> FEATURE:
<223> OTHER INFORMATION: PHM1192-4 Probe-2

<400> SEQUENCE: 8
acggacgcgg agcgctcatc agctaagaat 30

<210> SEQ ID NO 9
<211> LENGTH: 33
<212> TYPE: DNA
<213> ORGANISM: Artificial sequence
<220> FEATURE:
<223> OTHER INFORMATION: C00435-802 FW primer

<400> SEQUENCE: 9
yggtgataam attttcaacc tgtatgcctt gga 33

<210> SEQ ID NO 10
<211> LENGTH: 34
<212> TYPE: DNA
<213> ORGANISM: Artificial sequence
<220> FEATURE:
<223> OTHER INFORMATION: C00435-802 RV primer

<400> SEQUENCE: 10
gcctattcga taccaaaaac ttttcaaaga ctgc 34

<210> SEQ ID NO 11
<211> LENGTH: 29
<212> TYPE: DNA
<213> ORGANISM: Artificial sequence
<220> FEATURE:
<223> OTHER INFORMATION: C00435-802 Probe-1

<400> SEQUENCE: 11
acggacgcgg agtatgcaca tgtcaccat 29

<210> SEQ ID NO 12
<211> LENGTH: 26
<212> TYPE: DNA
<213> ORGANISM: Artificial sequence
<220> FEATURE:
<223> OTHER INFORMATION: C00435-802 Probe-2

<400> SEQUENCE: 12
cgcgccgagg aatgcacatg tcacca 26

<210> SEQ ID NO 13
<211> LENGTH: 34
<212> TYPE: DNA
<213> ORGANISM: Artificial sequence
<220> FEATURE:
<223> OTHER INFORMATION: C00436-801 FW primer

<400> SEQUENCE: 13
gctacgaaga ttgtccatat gacacagatg attc 34

<210> SEQ ID NO 14
<211> LENGTH: 34
<212> TYPE: DNA
<213> ORGANISM: Artificial sequence
<220> FEATURE:
<223> OTHER INFORMATION: C00436-801 RV primer

<400> SEQUENCE: 14
cctcggaaga ttcatcagga taatcaaaaa gagg 34

<210> SEQ ID NO 15
<211> LENGTH: 33
<212> TYPE: DNA
<213> ORGANISM: Artificial sequence
<220> FEATURE:
<223> OTHER INFORMATION: C00436-801 Probe-1

<400> SEQUENCE: 15
acggacgcgg agtagcttca gctaattcaa gta 33

<210> SEQ ID NO 16
<211> LENGTH: 29
<212> TYPE: DNA
<213> ORGANISM: Artificial sequence
<220> FEATURE:
<223> OTHER INFORMATION: C00423-801 Probe-2

<400> SEQUENCE: 16
cgcgccgagg gagcttcagc taattcaag 29

<210> SEQ ID NO 17
<211> LENGTH: 33
<212> TYPE: DNA
<213> ORGANISM: Artificial sequence
<220> FEATURE:
<223> OTHER INFORMATION: PHM187-7 FW primer

<400> SEQUENCE: 17
agttttgggt tttctwttgr aaggtggaag cca 33

<210> SEQ ID NO 18
<211> LENGTH: 22
<212> TYPE: DNA
<213> ORGANISM: Artificial sequence
<220> FEATURE:
<223> OTHER INFORMATION: PHM187-7 RV primer

<400> SEQUENCE: 18
acagactaac cgtgcccctt gt 22

<210> SEQ ID NO 19
<211> LENGTH: 25
<212> TYPE: DNA
<213> ORGANISM: Artificial sequence
<220> FEATURE:
<223> OTHER INFORMATION: PHM187-7 Probe-1

<400> SEQUENCE: 19
cgcgccgagg gcagctgagg agagt 25

<210> SEQ ID NO 20
<211> LENGTH: 28
<212> TYPE: DNA
<213> ORGANISM: Artificial sequence
<220> FEATURE:
<223> OTHER INFORMATION: PHM187-7 Probe-2

<400> SEQUENCE: 20
acggacgcgg agacagctga ggagagtg 28

<210> SEQ ID NO 21
<211> LENGTH: 23
<212> TYPE: DNA
<213> ORGANISM: Artificial sequence
<220> FEATURE:
<223> OTHER INFORMATION: C00423-801 FW primer

<400> SEQUENCE: 21
cagcatcgta cgtgttctgg cac 23

<210> SEQ ID NO 22
<211> LENGTH: 35
<212> TYPE: DNA
<213> ORGANISM: Artificial sequence
<220> FEATURE:
<223> OTHER INFORMATION: C00423-801 RV primer

<400> SEQUENCE: 22
ggctggtggt gtatttgtta yctctycatg ttcat 35

<210> SEQ ID NO 23
<211> LENGTH: 38
<212> TYPE: DNA
<213> ORGANISM: Artificial sequence
<220> FEATURE:
<223> OTHER INFORMATION: C00423-801 Probe-1

<400> SEQUENCE: 23
acggacgcgg agagtcataa tatttagtgt cttttctg 38

<210> SEQ ID NO 24
<211> LENGTH: 35
<212> TYPE: DNA
<213> ORGANISM: Artificial sequence
<220> FEATURE:
<223> OTHER INFORMATION: C00423-801 Probe-2

<400> SEQUENCE: 24
cgcgccgagg ggtcataata tttagtgtct tttct 35

<210> SEQ ID NO 25
<211> LENGTH: 30
<212> TYPE: DNA
<213> ORGANISM: Artificial sequence
<220> FEATURE:
<223> OTHER INFORMATION: PHM5028-24 FW primer

<400> SEQUENCE: 25
tcggctcatg tgagagtgtc ttcttaatga 30

<210> SEQ ID NO 26
<211> LENGTH: 31
<212> TYPE: DNA
<213> ORGANISM: Artificial sequence
<220> FEATURE:
<223> OTHER INFORMATION: PHM5028-24 RV primer

<400> SEQUENCE: 26
ctgcatattc ggtatggaaa kagcttcagc t 31

<210> SEQ ID NO 27

<211> LENGTH: 29
<212> TYPE: DNA
<213> ORGANISM: Artificial sequence
<220> FEATURE:
<223> OTHER INFORMATION: PHM5028-24 Probe-1

<400> SEQUENCE: 27
cgcgccgagg tgaatgctac gaagattgt 29

<210> SEQ ID NO 28
<211> LENGTH: 31
<212> TYPE: DNA
<213> ORGANISM: Artificial sequence
<220> FEATURE:
<223> OTHER INFORMATION: PHM5028-24 Probe-2

<400> SEQUENCE: 28
acggacgcgg agcgaatgct acgaagattg t 31

<210> SEQ ID NO 29
<211> LENGTH: 27
<212> TYPE: DNA
<213> ORGANISM: Artificial sequence
<220> FEATURE:
<223> OTHER INFORMATION: PHM13818-15 FW primer

<400> SEQUENCE: 29
aaggacatca tcctagaaga tgtcgcg 27

<210> SEQ ID NO 30
<211> LENGTH: 22
<212> TYPE: DNA
<213> ORGANISM: Artificial sequence
<220> FEATURE:
<223> OTHER INFORMATION: PHM13818-15 rv primer

<400> SEQUENCE: 30
actggtcccg atcaggaaac ca 22

<210> SEQ ID NO 31
<211> LENGTH: 24
<212> TYPE: DNA
<213> ORGANISM: Artificial sequence
<220> FEATURE:
<223> OTHER INFORMATION: PHM13818-15 Probe-1

<400> SEQUENCE: 31
cgcgccgagg tggcctgatg gtga 24

<210> SEQ ID NO 32
<211> LENGTH: 26
<212> TYPE: DNA
<213> ORGANISM: Artificial sequence
<220> FEATURE:
<223> OTHER INFORMATION: PHM13818-15 Probe-2

<400> SEQUENCE: 32
acggacgcgg agcggcctga tggtga 26

<210> SEQ ID NO 33
<211> LENGTH: 19
<212> TYPE: DNA
<213> ORGANISM: Artificial sequence
<220> FEATURE:
<223> OTHER INFORMATION: PHM15721-39 FW primer

<400> SEQUENCE: 33
gctctcgcgc cgayctcca 19

<210> SEQ ID NO 34
<211> LENGTH: 17
<212> TYPE: DNA
<213> ORGANISM: Artificial sequence
<220> FEATURE:
<223> OTHER INFORMATION: PHM15721-39 RV primer

<400> SEQUENCE: 34
ccgtcgccga tcccact 17

<210> SEQ ID NO 35
<211> LENGTH: 24
<212> TYPE: DNA
<213> ORGANISM: Artificial sequence
<220> FEATURE:
<223> OTHER INFORMATION: PHM15721-39 Probe-1

<400> SEQUENCE: 35
cgcgccgagg agatgatcgc cggc 24

<210> SEQ ID NO 36
<211> LENGTH: 27
<212> TYPE: DNA
<213> ORGANISM: Artificial sequence
<220> FEATURE:
<223> OTHER INFORMATION: PHM15721-39 Probe-2

<400> SEQUENCE: 36
acggacgcgg agacgaagat gatcgcc 27

<210> SEQ ID NO 37
<211> LENGTH: 20
<212> TYPE: DNA
<213> ORGANISM: Artificial sequence
<220> FEATURE:
<223> OTHER INFORMATION: PHM15721-180 FW primer

<400> SEQUENCE: 37
cgttggcgac gatgcatcgt 20

<210> SEQ ID NO 38
<211> LENGTH: 30
<212> TYPE: DNA
<213> ORGANISM: Artificial sequence
<220> FEATURE:
<223> OTHER INFORMATION: PHM15721-180 RV primer

<400> SEQUENCE: 38
tcgtagttgt tgatygcatt gggaatggag 30

<210> SEQ ID NO 39
<211> LENGTH: 25
<212> TYPE: DNA
<213> ORGANISM: Artificial sequence
<220> FEATURE:
<223> OTHER INFORMATION: PHM15721-180 Probe-1

<400> SEQUENCE: 39
cgcgccgagg gagccatgca acatg 25

<210> SEQ ID NO 40
<211> LENGTH: 28
<212> TYPE: DNA

<213> ORGANISM: Artificial sequence
<220> FEATURE:
<223> OTHER INFORMATION: PHM15721-180 Probe-2

<400> SEQUENCE: 40
acggacgcgg agaagccatg caacatgc 28

<210> SEQ ID NO 41
<211> LENGTH: 33
<212> TYPE: DNA
<213> ORGANISM: Artificial sequence
<220> FEATURE:
<223> OTHER INFORMATION: C00441-801 FW primer

<400> SEQUENCE: 41
tgatttgtas gaactcatag ctcatccact ggg 33

<210> SEQ ID NO 42
<211> LENGTH: 33
<212> TYPE: DNA
<213> ORGANISM: Artificial sequence
<220> FEATURE:
<223> OTHER INFORMATION: C00441-801 RV primer

<400> SEQUENCE: 42
gcatggaaaa agtacaagaa garagcaagg tga 33

<210> SEQ ID NO 43
<211> LENGTH: 28
<212> TYPE: DNA
<213> ORGANISM: Artificial sequence
<220> FEATURE:
<223> OTHER INFORMATION: C00441-801 Probe-1

<400> SEQUENCE: 43
acggacgcgg agactcaaga tcaacggc 28

<210> SEQ ID NO 44
<211> LENGTH: 26
<212> TYPE: DNA
<213> ORGANISM: Artificial sequence
<220> FEATURE:
<223> OTHER INFORMATION: C00441-801 Probe-2

<400> SEQUENCE: 44
cgcgccgagg tactcacgat caacgg 26

<210> SEQ ID NO 45
<211> LENGTH: 33
<212> TYPE: DNA
<213> ORGANISM: Artificial sequence
<220> FEATURE:
<223> OTHER INFORMATION: C00441-802 FW primer

<400> SEQUENCE: 45
tgatttgtas gaactcatag ctcatccact ggg 33

<210> SEQ ID NO 46
<211> LENGTH: 28
<212> TYPE: DNA
<213> ORGANISM: Artificial sequence
<220> FEATURE:
<223> OTHER INFORMATION: C00441-802 RV primer

<400> SEQUENCE: 46
acacttatgc acggaaaaga kgctgagc 28

<210> SEQ ID NO 47
<211> LENGTH: 32
<212> TYPE: DNA
<213> ORGANISM: Artificial sequence
<220> FEATURE:
<223> OTHER INFORMATION: C00441-802 Probe-1

<400> SEQUENCE: 47
acggacgcgg agaagcaagg tgatatccta ac 32

<210> SEQ ID NO 48
<211> LENGTH: 29
<212> TYPE: DNA
<213> ORGANISM: Artificial sequence
<220> FEATURE:
<223> OTHER INFORMATION: C00441-802 Probe-2

<400> SEQUENCE: 48
cgcgccgagg gagcaaggtg atatcctaa 29

<210> SEQ ID NO 49
<211> LENGTH: 20
<212> TYPE: DNA
<213> ORGANISM: Artificial sequence
<220> FEATURE:
<223> OTHER INFORMATION: PHM4370-19 FW primer

<400> SEQUENCE: 49
ggcygcagca gccrgttgga 20

<210> SEQ ID NO 50
<211> LENGTH: 21
<212> TYPE: DNA
<213> ORGANISM: Artificial sequence
<220> FEATURE:
<223> OTHER INFORMATION: PHM4370-19 RV primer

<400> SEQUENCE: 50
cggtggtgcg aayrggcctg g 21

<210> SEQ ID NO 51
<211> LENGTH: 27
<212> TYPE: DNA
<213> ORGANISM: Artificial sequence
<220> FEATURE:
<223> OTHER INFORMATION: PHM4370-19 Probe-1

<400> SEQUENCE: 51
cgcgccgagg gcacagatga accaagc 27

<210> SEQ ID NO 52
<211> LENGTH: 29
<212> TYPE: DNA
<213> ORGANISM: Artificial sequence
<220> FEATURE:
<223> OTHER INFORMATION: PHM4370-19 Probe-2

<400> SEQUENCE: 52
acggacgcgg agacacagat gaaccaagc 29

<210> SEQ ID NO 53
<211> LENGTH: 13
<212> TYPE: DNA
<213> ORGANISM: Artificial sequence
<220> FEATURE:

<223> OTHER INFORMATION: PHM731-107 FW primer

<400> SEQUENCE: 53
cgcctcgccg gcg 13

<210> SEQ ID NO 54
<211> LENGTH: 24
<212> TYPE: DNA
<213> ORGANISM: Artificial sequence
<220> FEATURE:
<223> OTHER INFORMATION: PHM731-107 RV primer

<400> SEQUENCE: 54
acttgtggtc gaaagggtcg atgt 24

<210> SEQ ID NO 55
<211> LENGTH: 24
<212> TYPE: DNA
<213> ORGANISM: Artificial sequence
<220> FEATURE:
<223> OTHER INFORMATION: PHM731-107 Probe-1

<400> SEQUENCE: 55
cgcgccgagg atcggtagcg tcgt 24

<210> SEQ ID NO 56
<211> LENGTH: 26
<212> TYPE: DNA
<213> ORGANISM: Artificial sequence
<220> FEATURE:
<223> OTHER INFORMATION: PHM731-107 Probe-2

<400> SEQUENCE: 56
acggacgcgg aggtcggtag cgtcgt 26

<210> SEQ ID NO 57
<211> LENGTH: 21
<212> TYPE: DNA
<213> ORGANISM: Artificial sequence
<220> FEATURE:
<223> OTHER INFORMATION: C00071-01 FW primer

<400> SEQUENCE: 57
gccaggccyr ttcgcaccac c 21

<210> SEQ ID NO 58
<211> LENGTH: 21
<212> TYPE: DNA
<213> ORGANISM: Artificial sequence
<220> FEATURE:
<223> OTHER INFORMATION: C00071-01 RV primer

<400> SEQUENCE: 58
ccagcgcttt gaccgaactg t 21

<210> SEQ ID NO 59
<211> LENGTH: 22
<212> TYPE: DNA
<213> ORGANISM: Artificial sequence
<220> FEATURE:
<223> OTHER INFORMATION: C00071-01 Probe-1

<400> SEQUENCE: 59
cgcgccgagg cgttgccgcc tc 22

```
<210> SEQ ID NO 60
<211> LENGTH: 24
<212> TYPE: DNA
<213> ORGANISM: Artificial sequence
<220> FEATURE:
<223> OTHER INFORMATION: C00071-01 Probe-2

<400> SEQUENCE: 60

acggacgcgg agcaccgttg ccgc                                            24


<210> SEQ ID NO 61
<211> LENGTH: 27
<212> TYPE: DNA
<213> ORGANISM: Artificial sequence
<220> FEATURE:
<223> OTHER INFORMATION: PHM8249-21 FW

<400> SEQUENCE: 61

agatcaagga catcttcatg cgctacg                                         27


<210> SEQ ID NO 62
<211> LENGTH: 15
<212> TYPE: DNA
<213> ORGANISM: Artificial sequence
<220> FEATURE:
<223> OTHER INFORMATION: PHM8249-21 RV primer

<400> SEQUENCE: 62

tgggctcgca gcggc                                                      15


<210> SEQ ID NO 63
<211> LENGTH: 21
<212> TYPE: DNA
<213> ORGANISM: Artificial sequence
<220> FEATURE:
<223> OTHER INFORMATION: PHM8249-21 Probe-1

<400> SEQUENCE: 63

cgcgccgagg tgccgacccc c                                               21


<210> SEQ ID NO 64
<211> LENGTH: 23
<212> TYPE: DNA
<213> ORGANISM: Artificial sequence
<220> FEATURE:
<223> OTHER INFORMATION: PHM8249-21 Probe-2

<400> SEQUENCE: 64

acggacgcgg agcgccgacc ccc                                             23


<210> SEQ ID NO 65
<211> LENGTH: 35
<212> TYPE: DNA
<213> ORGANISM: Artificial sequence
<220> FEATURE:
<223> OTHER INFORMATION: C00428-801 FW primer

<400> SEQUENCE: 65

agtatttcta acgctaaaat ccatggttgc tttca                                35


<210> SEQ ID NO 66
<211> LENGTH: 35
<212> TYPE: DNA
<213> ORGANISM: Artificial sequence
<220> FEATURE:
<223> OTHER INFORMATION: C00428-801 RV primer
```

<400> SEQUENCE: 66
accggaggcg tagagarata yaaaatcttc agtgt 35

<210> SEQ ID NO 67
<211> LENGTH: 25
<212> TYPE: DNA
<213> ORGANISM: Artificial sequence
<220> FEATURE:
<223> OTHER INFORMATION: C00428-801 Probe-1

<400> SEQUENCE: 67
acggacgcgg aggccctgca gtcag 25

<210> SEQ ID NO 68
<211> LENGTH: 24
<212> TYPE: DNA
<213> ORGANISM: Artificial sequence
<220> FEATURE:
<223> OTHER INFORMATION: C00428-801 Probe-2

<400> SEQUENCE: 68
cgcgccgagg accctgcagt cagt 24

<210> SEQ ID NO 69
<211> LENGTH: 19
<212> TYPE: DNA
<213> ORGANISM: Artificial sequence
<220> FEATURE:
<223> OTHER INFORMATION: PHM18427-13 FW primer

<400> SEQUENCE: 69
ccacgcygmt gacccgccg 19

<210> SEQ ID NO 70
<211> LENGTH: 22
<212> TYPE: DNA
<213> ORGANISM: Artificial sequence
<220> FEATURE:
<223> OTHER INFORMATION: PHM18427-13 RV primer

<400> SEQUENCE: 70
gtcggcaaca agttgtcgtc gt 22

<210> SEQ ID NO 71
<211> LENGTH: 21
<212> TYPE: DNA
<213> ORGANISM: Artificial sequence
<220> FEATURE:
<223> OTHER INFORMATION: PHM18427-13 Probe-1

<400> SEQUENCE: 71
cgcgccgagg cccaccggcg g 21

<210> SEQ ID NO 72
<211> LENGTH: 25
<212> TYPE: DNA
<213> ORGANISM: Artificial sequence
<220> FEATURE:
<223> OTHER INFORMATION: PHM18427-13 Probe-2

<400> SEQUENCE: 72
acggacgcgg agctacccac cggcg 25

<210> SEQ ID NO 73
<211> LENGTH: 33

<212> TYPE: DNA
<213> ORGANISM: Artificial sequence
<220> FEATURE:
<223> OTHER INFORMATION: PHM9535-10 FW primer

<400> SEQUENCE: 73
tttggacaca gacccwgtaa ctttrtgatg cac 33

<210> SEQ ID NO 74
<211> LENGTH: 27
<212> TYPE: DNA
<213> ORGANISM: Artificial sequence
<220> FEATURE:
<223> OTHER INFORMATION: PHM9535-10 RV primer

<400> SEQUENCE: 74
rccacaagct tcgagttctt tgaagag 27

<210> SEQ ID NO 75
<211> LENGTH: 32
<212> TYPE: DNA
<213> ORGANISM: Artificial sequence
<220> FEATURE:
<223> OTHER INFORMATION: PHM9535-10 Probe-1

<400> SEQUENCE: 75
cgcgccgagg cattcrtgta aggcacatta tc 32

<210> SEQ ID NO 76
<211> LENGTH: 35
<212> TYPE: DNA
<213> ORGANISM: Artificial sequence
<220> FEATURE:
<223> OTHER INFORMATION: PHM9535-10 Probe-2

<400> SEQUENCE: 76
acggacgcgg agaattcrtg taaggcacat tatca 35

<210> SEQ ID NO 77
<211> LENGTH: 29
<212> TYPE: DNA
<213> ORGANISM: Artificial sequence
<220> FEATURE:
<223> OTHER INFORMATION: PHM9535-6 FW primer

<400> SEQUENCE: 77
ccgaaacaat aggctagaca grctcgtga 29

<210> SEQ ID NO 78
<211> LENGTH: 35
<212> TYPE: DNA
<213> ORGANISM: Artificial sequence
<220> FEATURE:
<223> OTHER INFORMATION: PHM9535-6 RV primer

<400> SEQUENCE: 78
tgaagagcta aatcgkcata agrggcaggt aaagt 35

<210> SEQ ID NO 79
<211> LENGTH: 34
<212> TYPE: DNA
<213> ORGANISM: Artificial sequence
<220> FEATURE:
<223> OTHER INFORMATION: PHM9535-6 Probe-1

<400> SEQUENCE: 79
cgcgccgagg tgtaactttr tgatgcactt tata 34

<210> SEQ ID NO 80
<211> LENGTH: 36
<212> TYPE: DNA
<213> ORGANISM: Artificial sequence
<220> FEATURE:
<223> OTHER INFORMATION: PHM9535-6 Probe-2

<400> SEQUENCE: 80
acggacgcgg agagtaactt trtgatgcac tttata 36

<210> SEQ ID NO 81
<211> LENGTH: 29
<212> TYPE: DNA
<213> ORGANISM: Artificial sequence
<220> FEATURE:
<223> OTHER INFORMATION: PHM9535-7 FW primer

<400> SEQUENCE: 81
aacaataggc tagacagrct cgtgaaggt 29

<210> SEQ ID NO 82
<211> LENGTH: 35
<212> TYPE: DNA
<213> ORGANISM: Artificial sequence
<220> FEATURE:
<223> OTHER INFORMATION: PHM9535-7 RV primer

<400> SEQUENCE: 82
tgaagagcta aatcgkcata agrggcaggt aaagt 35

<210> SEQ ID NO 83
<211> LENGTH: 38
<212> TYPE: DNA
<213> ORGANISM: Artificial sequence
<220> FEATURE:
<223> OTHER INFORMATION: PHM9535-7 Probe-1
<220> FEATURE:
<221> NAME/KEY: misc_feature
<222> LOCATION: (26)..(26)
<223> OTHER INFORMATION: n is a, c, g, or t

<400> SEQUENCE: 83
cgcgccgagg gtgatgcact ttatantttt acttttac 38

<210> SEQ ID NO 84
<211> LENGTH: 40
<212> TYPE: DNA
<213> ORGANISM: Artificial sequence
<220> FEATURE:
<223> OTHER INFORMATION: PHM9535-7 Probe-2
<220> FEATURE:
<221> NAME/KEY: misc_feature
<222> LOCATION: (28)..(28)
<223> OTHER INFORMATION: n is a, c, g, or t

<400> SEQUENCE: 84
acggacgcgg agatgatgca ctttatantt ttacttttac 40

<210> SEQ ID NO 85
<211> LENGTH: 20
<212> TYPE: DNA
<213> ORGANISM: Artificial sequence
<220> FEATURE:
<223> OTHER INFORMATION: PHM4003-13 FW primer

<400> SEQUENCE: 85
caaggcgatc tggacgcacc 20

<210> SEQ ID NO 86
<211> LENGTH: 23
<212> TYPE: DNA
<213> ORGANISM: Artificial sequence
<220> FEATURE:
<223> OTHER INFORMATION: PHM4003-13 FW primer

<400> SEQUENCE: 86
catggcgttc cagtcgttct ctg 23

<210> SEQ ID NO 87
<211> LENGTH: 31
<212> TYPE: DNA
<213> ORGANISM: Artificial sequence
<220> FEATURE:
<223> OTHER INFORMATION: PHM4003-13 FW primer

<400> SEQUENCE: 87
cgcgccgagg aaactcaaag ttcctcagta g 31

<210> SEQ ID NO 88
<211> LENGTH: 32
<212> TYPE: DNA
<213> ORGANISM: Artificial sequence
<220> FEATURE:
<223> OTHER INFORMATION: PHM4003-13 FW primer

<400> SEQUENCE: 88
acggacgcgg aggaactcaa agttcctcag ta 32

<210> SEQ ID NO 89
<211> LENGTH: 492
<212> TYPE: DNA
<213> ORGANISM: Artificial sequence
<220> FEATURE:
<223> OTHER INFORMATION: PHM15590

<400> SEQUENCE: 89
cgtacgcccc agtcaaaagc cgttctcgga ggatgacttg cccaagatac cctacctgag 60
agctgtggtg ctggagggtc tccggcgcca tccgccgggg caccagatgc cgccacgcag 120
ggtgagggag gacgtggagg tgggtgacta cgtggtgccc aagggctcag cgatcaactt 180
catgctgtac gacctgggca tggacgacgc cacgtgggac cgcccagcag tgttcatgcc 240
ggagaggttc ctgcccggcg gggaagccga ggcgctggac atcaccggca ccaaggagat 300
gaagatgata ccgtttgggg cgggcagaag gatctgcccg ggcctcagga tcgctctcct 360
gctcctcgag tacttcgtcg ccaacctcgt agcgaccttc cactggaaag aggtggaaga 420
gggcgacgtc gatgtcacca ccgagacgct cagctcaccg tcctcatgga agccctcgaa 480
tttggaaaaa cc 492

<210> SEQ ID NO 90
<211> LENGTH: 552
<212> TYPE: DNA
<213> ORGANISM: Artificial sequence
<220> FEATURE:
<223> OTHER INFORMATION: PHM13818

<400> SEQUENCE: 90
aggggaaagg acccagtcag aacgctaaca tcagtgtttc caatgaggct ttcttccacc 60

```
aattcctcgc ggtgcgagcc atggatcctc tggatgtcct gagccagaac cccgattcag    120

tattcggaaa gttctgcaga agcaagtacc tatcgcttgt gcatcaaaaa atggaaggtt    180

ctttcttcgg caacgtggat cagaggaact acgtcatgag cggcggccat ccaaggacac    240

ctttctacca ggcattccta aagctagcaa agtccatatg gttgctgcac aggttggcgc    300

actccttcga tccaaaggca aaggtgtttc aagtgaaaaa gggaagtgaa ttttcggata    360

tccacatgga gagcgtcgtg aaggacatca tcctagaaga tgtcgcggag aggccgaaag    420

tcggcctgat ggtgacgcct ggtttcctga tcgggaccag tatcatacag tcccgtgtgt    480

acctttcagg tgccaagtgt gctgactgac tgactgaaga tgcagcagta cacaaatttg    540

gatataaaaa aa                                                         552
```

```
<210> SEQ ID NO 91
<211> LENGTH: 576
<212> TYPE: DNA
<213> ORGANISM: Artificial sequence
<220> FEATURE:
<223> OTHER INFORMATION: PHM1192

<400> SEQUENCE: 91

cccagtcaca acgggttaat gagaagctgc acagcctgca tggtgtaagt tgctctcaca     60

tgcttgttta tttacagaga aatatatatt gcgtgcttcg cttaaggcat atatacagac    120

ttggataatg tatgtgcaga tataaattga atgagtgttg ggtcactaca tgtaacatgc    180

tattattgta attaacaggt ggcaacaagg tgcaatgatc ctcagctgat agacttcatc    240

gagagtgagt tcctcgagga gcaggtataa aataaaatgc taccaacaag cttatatatg    300

ttcgttccgt atagtttaca cgacggaatt cttagctgat gagcgaaagt tttgggtttt    360

cttttggaag gtggaagcca taaataaggt ctccaagtat gtcgcacagc tgaggagagt    420

gggcaacaag ggcacggtt agtctgttgc taataaactt ggtttcatct gctatatatg    480

tctcgtgccc aaagttacga tattgttgag acgtggcttg cgtgcagggt gtgcacttga    540

tcagatgtgt acttttctag tactttggta rgcttg                               576
```

```
<210> SEQ ID NO 92
<211> LENGTH: 677
<212> TYPE: DNA
<213> ORGANISM: Artificial sequence
<220> FEATURE:
<223> OTHER INFORMATION: PHM187

<400> SEQUENCE: 92

acgtaatgag agctgaacag cctgcatggt gtaagttgct ctcacatgct tgtttattta     60

cagagaaata tatattgcgt gcttcgctta aggcatatat acagacttgg ataatgtatg    120

tgcagatata aattgaatga gtgttgggtc actacatgta acatgctatt attgtaatta    180

acaggtggca acaaggtgca atgatcctca gctgatagac ttcatcgaga gtgagttcct    240

cgaggagcag gtataaaata aaatgctacc aacaagctta tatatgttcg ttccgtatag    300

tttacacgac ggaattctta gctgatgagc gaaagttttg ggttttcttt tgaaaggtgg    360

aagccataaa taaggtctcc aagtatgtcg cacagctgag gagagtgggc aacaaggggc    420

acggttagtc tgttgctaat aaacttggtt tcatctgcta tatatgtctc gtgcccaaag    480

ttacgatatt gttgagacgt ggcttgcgtg caggggtgtg gcactttgat cagatgctgc    540

ttcaggaagg ggcctgaagg ccaacaaggg tggcgtggac ggagctgagc tctgggtggt    600

gtattctttt ctttttcttt tcttccagtt ggttagtgtt ttagttgtag aacggtgttg    660
```

cgtgcccaca tacatgg 677

<210> SEQ ID NO 93
<211> LENGTH: 732
<212> TYPE: DNA
<213> ORGANISM: Artificial sequence
<220> FEATURE:
<223> OTHER INFORMATION: PHM5028

<400> SEQUENCE: 93
ccatggaatg gagttgtacg tttcaagttt ccttacaaaa ttcactgcag gattacatct 60
tttgaagagg gtgctgttct atgcaacttt cttccactta tacgggaata cttgccatca 120
actgccgagg aaattgaggc ggatataatt tcattggcgc aatcagaagg tattgaagct 180
tgttgccttg agatgctctc aacagtaacg gaagggttct tggcgctttc tttattaact 240
gtaatactag cgaccaagta gtaatggtga acaatctagc tccagcatta attttgacga 300
gtctattttt gctgtttagc agattctgaa gtttatgata tctatactgt caaggaggtg 360
gatgacacaa tggaggccac gtcagcagct tcatatccaa ggtgaataac caaatatgaa 420
tcacatgtgt tttattcaat tcggctcatg tgagagtgtc ttcttaatga gtggtcttgt 480
tacataaggt tacaagtgga tgatggagaa gatgaatgct acgaagattg tccatatgac 540
acagatgatt cgaatggtaa ccgtaccatc attatttttc gttaactaat cagttagatc 600
catagctgct tgaattagct gaagctcttt ccataccgaa tatgcagccg aagacatcct 660
ctttttgatt atcctgatga atcttccgag gacgaggatg atgtagaacg acggagtcta 720
ggcttgttta gt 732

<210> SEQ ID NO 94
<211> LENGTH: 555
<212> TYPE: DNA
<213> ORGANISM: Artificial sequence
<220> FEATURE:
<223> OTHER INFORMATION: PHM4370

<400> SEQUENCE: 94
gatcacatca ccttccctcc agacactctc ggggcacgcc gggcttcagg tcgaaaagag 60
gcccaggctt gagagaccgt gctggccagc gacatgggcg cgcctccatt ctccgtgcaa 120
gcaccacggc tgcagcagcc ggttggagcg atgcccacac aagcagcggc acagatgaac 180
caagcgccag gcccattcgc accaccgcct ccaccaccac cgttgccgcc tcttctgcca 240
ccgctcctgc aacagttcgg tcaaagcgct ggaggaatga tggggatggg accgttcggg 300
atgatggctg gctccatgcc gcctcctccg ccgatgtcca gcatcatgcc agcaggtttt 360
ccagcgccaa gcggtccacc tccacctccg cttccaccgg ctcagaccca accccagcag 420
cagcagcagc agcattctcc tcctcaggcg ccagcacagc agcagccagc agggttcttc 480
cagccatcag caggcatggg gtacttccca gcagtgcagg tgcagcaatc tatggtcata 540
gctgttctat attca 555

<210> SEQ ID NO 95
<211> LENGTH: 534
<212> TYPE: DNA
<213> ORGANISM: Artificial sequence
<220> FEATURE:
<223> OTHER INFORMATION: PHM731

<400> SEQUENCE: 95

```
ccagtcacaa cggaagaagc tccggaagca gcaagccatc ggcgccatct tcgcgccacc     60

tcccccctcc gaacccaccg ccggccatgc cgattgccgt cgtcacgaca tgacccgctc    120

ctccaaggac agccacgctg cttgcccggc cgacagcaca ccagcggctg atgaggtcgt    180

cacccagctc atcgcccagc agttcgccgc caccgacggc gacacctcgt cgtcgtcgtc    240

gtactcgtac gcctccagca cggacaacat ctccaagctg ctcaacggct tcatgaagag    300

cgcctcgccg gcgcgggacg acgctaccga caccatcaag acttcctcgg ccattgacat    360

cgaccctttc gaccacaagt ccggcggggc actactacca ccacccaaga agcggcagca    420

gcagcagcag catctgtcct ccatagagaa ctggttgttc gacgatgcca ctggcaggtc    480

gttgtccagc tgatggagag atctccggcg ctcatgctca gtcccagcgt gtga          534
```

```
<210> SEQ ID NO 96
<211> LENGTH: 699
<212> TYPE: DNA
<213> ORGANISM: Artificial sequence
<220> FEATURE:
<223> OTHER INFORMATION: PHM15721
<220> FEATURE:
<221> NAME/KEY: misc_feature
<222> LOCATION: (8)..(8)
<223> OTHER INFORMATION: n is a, c, g, or t

<400> SEQUENCE: 96

tgaacgantm gcgcgagcga cgcacttttc atccccccctg tcgttcgccg cgcagcagac     60

ggcgcacggc atggccagca ggaacaaggc ggcggcgctg ctcctctgct tcctgttcct    120

ggccgcggtc gtcgcctccg ccgccgaggt gtgtgtatat ataatatatg catgctgcac    180

tggttgtgag ttgcaacaag cgttggcgac gatgcatcgt ttttatgatt ttatatatct    240

ctctgcttgc atgttgcatg gctctgctct cgcgccgatc tccattccca atgcgatcaa    300

caactacgaa cgaagatgat cgccggcagt gggatcggcg acggcgaagg tgaagagctg    360

gacaagggcg gcggcggcgg cggcggccac cacaagcacg aggtaataaa cgatacagtc    420

tgactgagct gacgactgga tcggatcgga tcggatcgga ggacgagcac gagagatgga    480

tgagaacctg ggaaatgatg agctgacacg catctgctgt tgtgcagggc tacaagaaca    540

aggatggcaa gggaaacctg aagccctctc gtaagtcgtt cttcggcttt cagctttgtt    600

cagtttttct tcttcttctt cgctgcaatc gcccaaaaca cgggcatccc gctaactcgg    660

cattttcccy tgcggtcatc gttaaacttt tcttctgcc                           699
```

```
<210> SEQ ID NO 97
<211> LENGTH: 21
<212> TYPE: DNA
<213> ORGANISM: Artificial sequence
<220> FEATURE:
<223> OTHER INFORMATION: PHM15590 F46

<400> SEQUENCE: 97

aggagatgat ggtgaaagcc a                                               21
```

```
<210> SEQ ID NO 98
<211> LENGTH: 20
<212> TYPE: DNA
<213> ORGANISM: Artificial sequence
<220> FEATURE:
<223> OTHER INFORMATION: PHM15590 F99

<400> SEQUENCE: 98

ccgttctcgg aggatgactt                                                 20
```

<210> SEQ ID NO 99
<211> LENGTH: 18
<212> TYPE: DNA
<213> ORGANISM: Artificial sequence
<220> FEATURE:
<223> OTHER INFORMATION: PHM15590 R563

<400> SEQUENCE: 99
ccggagcggc ttccccat 18

<210> SEQ ID NO 100
<211> LENGTH: 22
<212> TYPE: DNA
<213> ORGANISM: Artificial sequence
<220> FEATURE:
<223> OTHER INFORMATION: PHM15590 R601

<400> SEQUENCE: 100
aattaagcag acgaatgcag tc 22

<210> SEQ ID NO 101
<211> LENGTH: 21
<212> TYPE: DNA
<213> ORGANISM: Artificial sequence
<220> FEATURE:
<223> OTHER INFORMATION: PHM13818 F51

<400> SEQUENCE: 101
aagaatgttc agtgggttcc a 21

<210> SEQ ID NO 102
<211> LENGTH: 22
<212> TYPE: DNA
<213> ORGANISM: Artificial sequence
<220> FEATURE:
<223> OTHER INFORMATION: PHM13818 F98

<400> SEQUENCE: 102
ctaacatcag tgtttccaat ga 22

<210> SEQ ID NO 103
<211> LENGTH: 20
<212> TYPE: DNA
<213> ORGANISM: Artificial sequence
<220> FEATURE:
<223> OTHER INFORMATION: PHM13818 R614

<400> SEQUENCE: 103
cttgtgtagc tgctgcatct 20

<210> SEQ ID NO 104
<211> LENGTH: 20
<212> TYPE: DNA
<213> ORGANISM: Artificial sequence
<220> FEATURE:
<223> OTHER INFORMATION: PHM13818 R665

<400> SEQUENCE: 104
ctctgaagct ctcccaagat 20

<210> SEQ ID NO 105
<211> LENGTH: 20
<212> TYPE: DNA
<213> ORGANISM: Artificial sequence
<220> FEATURE:

<223> OTHER INFORMATION: PHM1192 F83

<400> SEQUENCE: 105
atgggtttca gctatggagc 20

<210> SEQ ID NO 106
<211> LENGTH: 21
<212> TYPE: DNA
<213> ORGANISM: Artificial sequence
<220> FEATURE:
<223> OTHER INFORMATION: PHM1192 F125

<400> SEQUENCE: 106
ggttaatgag aagctgcaca g 21

<210> SEQ ID NO 107
<211> LENGTH: 21
<212> TYPE: DNA
<213> ORGANISM: Artificial sequence
<220> FEATURE:
<223> OTHER INFORMATION: PHM1192 R668

<400> SEQUENCE: 107
gaagcagcat ctgatcaaag t 21

<210> SEQ ID NO 108
<211> LENGTH: 20
<212> TYPE: DNA
<213> ORGANISM: Artificial sequence
<220> FEATURE:
<223> OTHER INFORMATION: PHM1192 R801

<400> SEQUENCE: 108
catcatgtca tgtgggcaac 20

<210> SEQ ID NO 109
<211> LENGTH: 19
<212> TYPE: DNA
<213> ORGANISM: Artificial sequence
<220> FEATURE:
<223> OTHER INFORMATION: PHM187 F1265

<400> SEQUENCE: 109
gagctgactc tggctctgg 19

<210> SEQ ID NO 110
<211> LENGTH: 20
<212> TYPE: DNA
<213> ORGANISM: Artificial sequence
<220> FEATURE:
<223> OTHER INFORMATION: PHM187 F1294

<400> SEQUENCE: 110
taatgagaag ctgcacagcc 20

<210> SEQ ID NO 111
<211> LENGTH: 20
<212> TYPE: DNA
<213> ORGANISM: Artificial sequence
<220> FEATURE:
<223> OTHER INFORMATION: PHM187 R1975

<400> SEQUENCE: 111
tccatcatgt catgtgggca 20

<210> SEQ ID NO 112
<211> LENGTH: 20
<212> TYPE: DNA
<213> ORGANISM: Artificial sequence
<220> FEATURE:
<223> OTHER INFORMATION: PHM187 R1996

<400> SEQUENCE: 112
gagacaatcc tccacgtaac 20

<210> SEQ ID NO 113
<211> LENGTH: 22
<212> TYPE: DNA
<213> ORGANISM: Artificial sequence
<220> FEATURE:
<223> OTHER INFORMATION: PHM5028 F370

<400> SEQUENCE: 113
catgaggata tgggaagaaa tg 22

<210> SEQ ID NO 114
<211> LENGTH: 21
<212> TYPE: DNA
<213> ORGANISM: Artificial sequence
<220> FEATURE:
<223> OTHER INFORMATION: PHM5028 F409

<400> SEQUENCE: 114
tggaagagtc gaaaaggaga a 21

<210> SEQ ID NO 115
<211> LENGTH: 20
<212> TYPE: DNA
<213> ORGANISM: Artificial sequence
<220> FEATURE:
<223> OTHER INFORMATION: PHM5028 R868

<400> SEQUENCE: 115
aaggatcctc gtcgttccta 20

<210> SEQ ID NO 116
<211> LENGTH: 21
<212> TYPE: DNA
<213> ORGANISM: Artificial sequence
<220> FEATURE:
<223> OTHER INFORMATION: PHM5028 R889

<400> SEQUENCE: 116
cagaaccttc tttgtctcca a 21

<210> SEQ ID NO 117
<211> LENGTH: 21
<212> TYPE: DNA
<213> ORGANISM: Artificial sequence
<220> FEATURE:
<223> OTHER INFORMATION: PHM4370 F272

<400> SEQUENCE: 117
tatcttccat gaacagcgga t 21

<210> SEQ ID NO 118
<211> LENGTH: 20
<212> TYPE: DNA
<213> ORGANISM: Artificial sequence
<220> FEATURE:
<223> OTHER INFORMATION: PHM4370 F294

<400> SEQUENCE: 118
tcctcccaga gaccaactct 20

<210> SEQ ID NO 119
<211> LENGTH: 19
<212> TYPE: DNA
<213> ORGANISM: Artificial sequence
<220> FEATURE:
<223> OTHER INFORMATION: PHM4370 R810

<400> SEQUENCE: 119
agattgctgc acctgcact 19

<210> SEQ ID NO 120
<211> LENGTH: 20
<212> TYPE: DNA
<213> ORGANISM: Artificial sequence
<220> FEATURE:
<223> OTHER INFORMATION: PHM4370 R848

<400> SEQUENCE: 120
gtcatgccac catagagtca 20

<210> SEQ ID NO 121
<211> LENGTH: 19
<212> TYPE: DNA
<213> ORGANISM: Artificial sequence
<220> FEATURE:
<223> OTHER INFORMATION: PHM731 F301

<400> SEQUENCE: 121
ctccaggcct tgctaggca 19

<210> SEQ ID NO 122
<211> LENGTH: 19
<212> TYPE: DNA
<213> ORGANISM: Artificial sequence
<220> FEATURE:
<223> OTHER INFORMATION: PHM731 F399

<400> SEQUENCE: 122
gaagaagctc cggaagcag 19

<210> SEQ ID NO 123
<211> LENGTH: 21
<212> TYPE: DNA
<213> ORGANISM: Artificial sequence
<220> FEATURE:
<223> OTHER INFORMATION: PHM731 R926

<400> SEQUENCE: 123
taaagcagca tgggaactga g 21

<210> SEQ ID NO 124
<211> LENGTH: 22
<212> TYPE: DNA
<213> ORGANISM: Artificial sequence
<220> FEATURE:
<223> OTHER INFORMATION: PHM731 R948

<400> SEQUENCE: 124
cgcttctttt tcttggtgct aa 22

<210> SEQ ID NO 125
<211> LENGTH: 21

<212> TYPE: DNA
<213> ORGANISM: Artificial sequence
<220> FEATURE:
<223> OTHER INFORMATION: PHM15721 F51

<400> SEQUENCE: 125
gtgcgtgtca cactcactga t 21

<210> SEQ ID NO 126
<211> LENGTH: 20
<212> TYPE: DNA
<213> ORGANISM: Artificial sequence
<220> FEATURE:
<223> OTHER INFORMATION: PHM15721 F90

<400> SEQUENCE: 126
tactccttcc cttgtccgtt 20

<210> SEQ ID NO 127
<211> LENGTH: 19
<212> TYPE: DNA
<213> ORGANISM: Artificial sequence
<220> FEATURE:
<223> OTHER INFORMATION: PHM15721 R550

<400> SEQUENCE: 127
tattgggccg ccatcttct 19

<210> SEQ ID NO 128
<211> LENGTH: 21
<212> TYPE: DNA
<213> ORGANISM: Artificial sequence
<220> FEATURE:
<223> OTHER INFORMATION: PHM15721 R611

<400> SEQUENCE: 128
actacggtgg taggttacga t 21

<210> SEQ ID NO 129
<211> LENGTH: 22
<212> TYPE: DNA
<213> ORGANISM: Artificial sequence
<220> FEATURE:
<223> OTHER INFORMATION: Ct9050c497L12e PL

<400> SEQUENCE: 129
gagccatgct gctttattcg at 22

<210> SEQ ID NO 130
<211> LENGTH: 23
<212> TYPE: DNA
<213> ORGANISM: Artificial sequence
<220> FEATURE:
<223> OTHER INFORMATION: Ct9050c497L12e PR

<400> SEQUENCE: 130
cacgctcatc aacaacacat gat 23

<210> SEQ ID NO 131
<211> LENGTH: 22
<212> TYPE: DNA
<213> ORGANISM: Artificial sequence
<220> FEATURE:
<223> OTHER INFORMATION: Ct9050c064G11d PL

<400> SEQUENCE: 131

```
ctgagctgat tgattgcacc ac                                              22


<210> SEQ ID NO 132
<211> LENGTH: 22
<212> TYPE: DNA
<213> ORGANISM: Artificial sequence
<220> FEATURE:
<223> OTHER INFORMATION: Ct9050c064G11d PR

<400> SEQUENCE: 132

atcgaaaacc agacagcacc at                                              22


<210> SEQ ID NO 133
<211> LENGTH: 22
<212> TYPE: DNA
<213> ORGANISM: Artificial sequence
<220> FEATURE:
<223> OTHER INFORMATION: Ct9050c064G11c PL

<400> SEQUENCE: 133

tgtcgactgt cttcgtcgtc at                                              22


<210> SEQ ID NO 134
<211> LENGTH: 22
<212> TYPE: DNA
<213> ORGANISM: Artificial sequence
<220> FEATURE:
<223> OTHER INFORMATION: Ct9050c064G11c PR

<400> SEQUENCE: 134

cacgctgtgt gtgtaggtag gc                                              22


<210> SEQ ID NO 135
<211> LENGTH: 20
<212> TYPE: DNA
<213> ORGANISM: Artificial sequence
<220> FEATURE:
<223> OTHER INFORMATION: Ct9050b191E02m PL

<400> SEQUENCE: 135

cagtctctgc ctccgtctcg                                                 20


<210> SEQ ID NO 136
<211> LENGTH: 26
<212> TYPE: DNA
<213> ORGANISM: Artificial sequence
<220> FEATURE:
<223> OTHER INFORMATION: Ct9050b191E02m PR

<400> SEQUENCE: 136

acccacaaaa ctatcagtgt gctaag                                          26


<210> SEQ ID NO 137
<211> LENGTH: 726
<212> TYPE: DNA
<213> ORGANISM: Artificial sequence
<220> FEATURE:
<223> OTHER INFORMATION: PHS6Y
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
```

<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t

<400> SEQUENCE: 137
nnnnnnnnnn nnnnnnnnnn ntcgttgcgc cngcaccagc accngcacca ccngaaccng 60
agaacgacga cgagtcgacg accattcccc gccgtacgac gccnacgtgg taccgccttc 120
gccgctagct ccggccggcc gggaagcagt cgtcgcggcc gccacgtaga gggacggacc 180
acccttcgaa taatagttag cccgggactt ggcacgttct agttggaaca gagacaacgg 240
agccagacgt acggatcttg aatccacaag agagcaaaac tctctctctg tatccatctc 300
atgcaatggt tttagttagg ccctgtttca atctcatggg ataaagttta gcttcctgct 360
aaactttagc tatatgaatt gaagtgctaa agtttagctt caattaccac cattagctct 420
cctgtttaga ttacaaatgg ctaaaagtag ctaaaaaata gctgctaaag tttatctcgc 480
gagattgaaa caggccctta gctcagttga tgagtttttt tagttagctc caaatccttg 540
ctgactgcta gctagggcgc tgctaggcag ctggctcgct tttccaaaga aacaacgctc 600
ctaattaatt tggttggagg ggcaaatctt gtcttgtcag cagctaacgc acacgtgatg 660
tgtgtgtgtg tacggtgtgc ccctaccgga ccccagcttg gccnnctacc tcnctcgcgc 720 cnttan 726

<210> SEQ ID NO 138
<211> LENGTH: 723
<212> TYPE: DNA
<213> ORGANISM: Artificial sequence
<220> FEATURE:
<223> OTHER INFORMATION: PH1JG22
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:

<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (721)..(723)
<223> OTHER INFORMATION: n is a, c, g, or t

<400> SEQUENCE: 138
nnnnnnnnnn nnnnnnnnnn nncgttgcgc cngcaccngc accngcacca ccngaaccng 60
agaacgacga cgagtcgacg accattcccc gccgtacgac gcccacgtgg taccgccttc 120
gccgctagct ccggccggcc gggaagcagt cgtcgcggcc gccacgtaga gggacggacc 180
acccttcgaa taatagttag cccgggactt ggcacgttct agttggaaca gagacaacgg 240
agccagacgt acggatcttg aatccacaag agagcaaaac tctctctctg tatccatctc 300
atgcaatggt tttagttagg ccctgtttca atctcatggg ataaagttta gcttcctgct 360
aaactttagc tatatgaatt gaagtgctaa agtttagctt caattaccac cattagctct 420
cctgtttaga ttacaaatgg ctaaaagtag ctaaaaaata gctgctaaag tttatctcgc 480
gagattgaaa caggccctta gctcagttga tgagtttttt tagttagctc cnaatccttg 540
ctgactgcta gctagggcgc tgctaggcag ctggctcgct tttccnaaga aacaacgctc 600
ctaattaatt tggttggagg ggcaaatctt gtcttgtcag cagctaacgc acacgtgatg 660
tgtgtgtgtg tacngtgtgc ccctaccgga ccccancttg gncnnctacc tcnctcgcgc 720 nnn 723

<210> SEQ ID NO 139
<211> LENGTH: 725
<212> TYPE: DNA
<213> ORGANISM: Artificial sequence
<220> FEATURE:
<223> OTHER INFORMATION: PH1FT71

<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (693)..(694)
<223> OTHER INFORMATION: n is a, c, g, or t
<220> FEATURE:
<221> NAME/KEY: misc_feature
<222> LOCATION: (703)..(704)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(725)
<223> OTHER INFORMATION: n is a, c, g, or t

<400> SEQUENCE: 139
nnnnnnnnnn nnnnnnnnnn tcgttgcgcc ngcaccngca ccngcaccac cngaaccnga 60
gaacgacgac gagtcgacga ccattccccg ccgtacgacg ccnacgtggt accgccttcg 120
ccgctagctc cggccggccg ggaagcagtc gtcgcggccg ccacgtagag ggacggacca 180
cccttcgaat aatagttagc ccgggacttg gcacgttcta gttggaacag agacaacgga 240

```
gccagacgta cggatcttga atccacaaga gagcaaaact ctctctctgt atccatctca    300

tgcaatggtt ttagttaggc cctgtttcaa tctcatggga taaagtttag cttcctgcta    360

aactttagct atatgaattg aagtgctaaa gtttagcttc aattaccacc attagctctc    420

ctgtttagat tacaaatggc taaaagtagc taaaaaatag ctgctaaagt ttatctcgcg    480

agattgaaac aggcccttag ctcagttgat gagttttttt agttagctcc aaatccttgc    540

tgactgctag ctagggcgct gctaggcagc tggctcgctt ttccnaagaa acaacgctcc    600

taattaattt ggttggaggg gcaaatcttg tcttgtcanc anctaacgca cacgtgatgt    660

gtgtgtgtgt acggtgtgcc cctaccggan ncnngcttgg ccnnctancn cgctcgcncn    720

nnnnn                                                                725
```

```
<210> SEQ ID NO 140
<211> LENGTH: 728
<212> TYPE: DNA
<213> ORGANISM: Artificial sequence
<220> FEATURE:
<223> OTHER INFORMATION: PH1G3H1
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
```

<222> LOCATION: (697)..(697)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t

<400> SEQUENCE: 140

```
nnnnnnnnnn nnnnnnnnnn nntcgttgcg ccngcaccng caccngcacc accngaaccn     60

gagaacgacg acnagtcgac gaccattccc cgccgtacga cgcccacgtg gtaccgcctt    120

cgccgctngc tccggccggc cgggaagcag tcgtcgcggc cgccacgtag agggacggac    180

caccccttcga ataatagtta gcccgggact tggcacgttc tagttggaac agagacnacg    240

gagccngacg tacggatctt gaatccacaa gagagcaaaa ctctctctct gtatccntct    300

catgcaatgg ttttagttag gccctgtttc aatctcatgg gataaagttt agcttcctgc    360

taaactttag ctatatgaat tgaagtgcta aagtttagct tcaattacca ccattagctc    420

tcctgtttag attacaaatg gctaaaagta gctaaaaaat agctgctaaa gtttatctcg    480

cgagattgaa acaggccctt agctcagttg atgagttttt ttagttagct ccnaatcctt    540

gctgactgct agctagggcg ctgctaggca gctggctcgc ttttccnaag aaacaacgct    600

cctaattaat ttggttggag gggcaaatct tgtcttgtca gcagctaacg cacacgtgat    660

gtgtgtgtgt gtacggtgtg cccctaccgg accccanctt ggccagctac ctcnctcgcg    720

ccnttacn                                                              728
```

<210> SEQ ID NO 141
<211> LENGTH: 725
<212> TYPE: DNA
<213> ORGANISM: Artificial sequence
<220> FEATURE:
<223> OTHER INFORMATION: PH1JG01
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:

<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (703)..(705)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (724)..(725)
<223> OTHER INFORMATION: n is a, c, g, or t

<400> SEQUENCE: 141
nnnnnnnnnn nnnnnnnnnn nncgttgcgc cngcaccngc accngcaccn ccngaaccng 60
agaacgacga cgagtcgacg accattcccc gccgtacgac gcccacgtgg taccgccttc 120
gccgctngct ccggccggcc gggaagcagt cgtcgcggcc gccacgtaga gggacggacc 180
acccttcgaa taatagttag cccgggactt ggcacgttct agttggaaca gagacaacgg 240
agccngacgt acggatcttg aatccacaag agagcaaaac tctctctctg tatccntctc 300
atgcaatggt tttagttagg ccctgtttca atctcatggg ataaagttta gcttcctgct 360
aaactttagc tatatgaatt gaagtgctaa agtttagctt caattaccac cattagctct 420

```
cctgtttaga ttacaaatgg ctaaaagtag ctaaaaaata gctgctaaag tttatctcgc    480

gagattgaaa caggccctta gctcagttga tgagtttttt tagttagctc cnaatccttg    540

ctgactgcta gctagggcgc tgctaggcag ctggctcgct tttccnaaga aacnacgctc    600

ctaattaatt tggttggagg ggcnaatctt gtcttgtcng cngctaacgc acacgtgatg    660

tgtgtgtgtg tacggtgtgc ccctaccgga ccccancttg gcnnnctacc tcnctcncnc    720

nntnn                                                                725
```

```
<210> SEQ ID NO 142
<211> LENGTH: 725
<212> TYPE: DNA
<213> ORGANISM: Artificial sequence
<220> FEATURE:
<223> OTHER INFORMATION: PHS7W
<220> FEATURE:
<221> NAME/KEY: misc_feature
<222> LOCATION: (2)..(22)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (688)..(689)
<223> OTHER INFORMATION: n is a, c, g, or t
<220> FEATURE:
<221> NAME/KEY: misc_feature
<222> LOCATION: (723)..(725)
<223> OTHER INFORMATION: n is a, c, g, or t

<400> SEQUENCE: 142

gnnnnnnnnn nnnnnnnnnn nncgttgcgc cngcaccngc accagcacca ccngaaccng     60

agaacgacga cgagtcgacg accattcccc gccgtacgac gcctacgtgg taccgccttc    120

gccgctagct ccggccggcc gggaagcagt cgtcgcggcc gccacgtaga gggacggacc    180

acccttcgaa taatagttag cccgggactt ggcacgttct agttggaaca gagacaacgg    240

agccagacgt acggatcttg aatccacaag agagcaaaac tctctctctg tatccatctc    300

atgcaatggt tttagttagg ccctgtttca atctcatggg ataaagttta gcttcctgct    360

aaactttagc tatatgaatt gaagtgctaa agtttagctt caattaccac cattagctct    420

cctgtttaga ttacaaatgg ctaaaagtag ctaaaaaata gctgctaaag tttatctcgc    480

gagattgaaa caggccctta gctcagttga tgagtttttt tagttagctc caaatccttg    540

ctgactgcta gctagggcgc tgctaggcag ctggctcgct tttccaaaga aacaacgctc    600

ctaattaatt tggttggagg ggcaaatctt gtcttgtcag cagctaacgc acacgtgatg    660

tgtgtgtgtg tacggtgtgc ccctaccnna ccccagcttg gccagctacc tcgctcgcgc    720

ctnnn                                                                725

<210> SEQ ID NO 143
```

<211> LENGTH: 724
<212> TYPE: DNA
<213> ORGANISM: Artificial sequence
<220> FEATURE:
<223> OTHER INFORMATION: PH7W3
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (684)..(689)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (708)..(711)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t

<400> SEQUENCE: 143

```
nnnnnnnnnn nnnnnntnnt cgttgcgccn gcaccagcac cagcaccacc ngaaccagag     60

aacgacgacg agtcgacgac cattccccgc cgtacgacgc cnacgtggta ccgccttcgc    120

cgctagctcc ggccggccgg gaagcagtcg tcgcggccgc cacgtagagg gacggaccac    180

ccttcgaata atagttagcc cgggacttgg cacgttctag ttggaacaga gacaacggag    240

ccagacgtac ggatcttgaa tccacaagag agcaaaactc tctctctgta tccatctcat    300

gcaatggttt tagttaggcc ctgtttcaat ctcatgggat aaagtttagc ttcctgctaa    360

actttagcta tatgaattga agtgctaaag tttagcttca attaccacca ttagctctcc    420

tgtttagatt acaaatggct aaaagtagct aaaaaatagc tgctaaagtt tatctcgcga    480

gattgaaaca ggcccttagc tcagttgatg agttttttt agttagctcc aaatccttgc     540

tgactgctag ctagggcgct gctaggcagc tggctcgctt ttccnaagaa acaacgctcc    600

taattaattt ggttggaggg gcaaatcttg tcttgtcagc agctaacgca cacgtgatgt    660

gtgtgtgtgt gtacggtgtg cccnnnnnng accccagctt ggccancnnn ntcgctcgcg    720

ccnn                                                                 724
```

<210> SEQ ID NO 144
<211> LENGTH: 757
<212> TYPE: DNA
<213> ORGANISM: Artificial sequence
<220> FEATURE:
<223> OTHER INFORMATION: PH9VF
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (753)..(757)
<223> OTHER INFORMATION: n is a, c, g, or t

<400> SEQUENCE: 144
nnnnnnnnnn nnnnnnnnnt tcgttgcgcc ngcaccngca ccngcaccac cngaaccaga 60
gaacgacgac gagtcgacga ccattccccg ccgtacgacg ccnacgtggt accgccttcg 120
ccgctagctc cggccggccg ggaagcagtc gtcgcggccg ccacgtagag ggacggacca 180
cccttcgaat aatagttagc ccgggacttg gcacgttcta gttggaacag agacaacgga 240
gccagacgta cggatcttga atccacaaga gagcaaaact ctctctctgt atccatctca 300
tgcaatggtt ttagttaggc cctgtttcaa tctcatggga taaagtttag cttcctgcta 360
aactttagct atatgaattg aagtgctaaa gtttagcttc aattaccacc attagctctc 420
ctgtttagat tacaaatggc taaaagtagc taaaaaatag ctgctaaagt ttatctcgcg 480
agattgaaac aggcccttag ctcagttgat gagttttttt tagttagctc caaatccttg 540
ctgactgcta gctagggcgc tgctaggcag ctggctcgct tttccaaaga aacaacgctc 600
ctaattaatt tggttggagg ggcaaatctt gtcttgtcag cagctaacgc acacgtgatg 660
tgtgtgtgtg tgtacggtgt gcccctaccn gaccccanct tggccagcta cctcgctcgc 720
gcctttacca gctagccnac cnacncacac agnnnnn 757

<210> SEQ ID NO 145
<211> LENGTH: 729
<212> TYPE: DNA
<213> ORGANISM: Artificial sequence
<220> FEATURE:
<223> OTHER INFORMATION: PHBNA
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(701)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t

<400> SEQUENCE: 145
nnnnnnnnnn nnnnnnnnnn ntcnntgcgc cngcnntagc accaggcacc nccngaacca 60
gagaacgacg acgagtcgac gaccattccc cgccgtacga cgccnacgtg gtaccgcctt 120
cgccgctagc tccggccggc cgggaagcag tcgtcgcggc cgccacgtag agggacggac 180 caccccttcga ataatagtta gcccgggact tggcacgttc tagttggaac agagacaacg 240
gagccagcag acgtacggat cttgaatcca caagagagca aaactctctc tctgtatcca 300
tctcatgcaa tggttttagt taggccctgt ttcaatctca tgggataaag tttagcttcc 360
tgctaaactt tagctatatg aattgaagtg ctaaagttta gcttcaatta ccaccattag 420

```
ctctcctgtt tagattacaa atggctaaaa gtagctaaaa aatagctgct aaagtttatc    480

tcgcgagatt gaaacaggcc cttagctcag ttgatgagtt ttttttagtt agctccaaat    540

ccttgctgac tgctagctag ggcgctgcta ggcagctggc tcgcttttcc aaagaaacaa    600

cgctcctaat taatttggtt ggaggggcaa atcttgtctt gtcannanct aacgcacacg    660

tgatgtgtgt gtgtgtacgg tgtgccccta ccgganccnn ncttggccag ctacctcgct    720

cgnnccntn                                                            729
```

<210> SEQ ID NO 146
<211> LENGTH: 748
<212> TYPE: DNA
<213> ORGANISM: Artificial sequence
<220> FEATURE:
<223> OTHER INFORMATION: PH2JR
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (697)..(704)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (711)..(712)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (720)..(720)

<223> OTHER INFORMATION: n is a, c, g, or t
<220> FEATURE:
<221> NAME/KEY: misc_feature
<222> LOCATION: (723)..(737)
<223> OTHER INFORMATION: n is a, c, g, or t
<220> FEATURE:
<221> NAME/KEY: misc_feature
<222> LOCATION: (739)..(744)
<223> OTHER INFORMATION: n is a, c, g, or t
<220> FEATURE:
<221> NAME/KEY: misc_feature
<222> LOCATION: (747)..(748)
<223> OTHER INFORMATION: n is a, c, g, or t

<400> SEQUENCE: 146

```
nnnnnnnnnn nnnnnnnnnn nntcgttgcg ccngcaccag caccngcacc accngaaccn     60

gagaacgacg acgagtcgac gaccattccc cgccgtacga cgccnacgtg gtaccgcctt    120

cgccgctagc tccggccggc cgggaagcag tcgtcgcggc cgccacgtag agggacggac    180

caccccttcga ataatagtta gcccgggact tggcacgttc tagttggaac agagacaacg    240

gagccagacg tacggatctt gaatccacaa gagagcaaaa ctctctctct gtatccatct    300

catgcaatgg ttttagttag gccctgtttc aatctcatgg gataaagttt agcttcctgc    360

taaactttag ctatatgaat tgaagtgcta aagtttagct tcaattacca ccattagctc    420

tcctgtttag attacaaatg gctaaaagta gctaaaaaat agctgctaaa gtttatctcg    480

cgagattgaa acaggccctt agctcagttg atgagttttt tttagttagc tccnaatcct    540

tgctgactgc tagctagggc gctgctaggc agctggctcg cttttccaaa gaaacaacgc    600

tcctaattaa tttggttgga ggggcaaatc ttgtcttgtc nncanctaac gcacacgtga    660

tgtgtgtgtg tgtacngtgt gcccctaccg gaccccnnnn nnnncnntac nncnctcgcn    720

ccnnnnnnnn nnnnnnnann nnnnaann                                       748
```

<210> SEQ ID NO 147
<211> LENGTH: 724
<212> TYPE: DNA
<213> ORGANISM: Artificial sequence
<220> FEATURE:
<223> OTHER INFORMATION: PH0TJ
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (27)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (694)..(696)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (709)..(710)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (717)..(718)
<223> OTHER INFORMATION: n is a, c, g, or t

<400> SEQUENCE: 147
nnnnnnnnnn nnnnnnnnnn ncgttgnnnn nnaccagcac cngcaccacc ngaaccngag 60
aacgacgacg agtcgacgac cattccccgc cgtacgacgc ccacgtggta ccgccttcgc 120
cgctagctcc ggccggccgg gaagcagtcg tcgcggccgc cacgtagagg gacggaccac 180
ccttcgaata atagttagcc cgggacttgg cacgttctag ttggaacaga gacaacggag 240
ccagacgtac ggatcttgaa tccacaagag agcaaaactc tctctctgta tccatctcat 300
gcaatggttt tagttaggcc ctgtttcaat ctcatgggat aaagtttagc ttcctgctaa 360
actttagcta tatgaattga agtgctaaag tttagcttca attaccacca ttagctctcc 420
tgtttagatt acaaatggct aaaagtagct aaaaaatagc tgctaaagtt tatctcgcga 480
gattgaaaca ggcccttagc tcagttgatg agttttttt agttagctcc naatccttgc 540
tgactgctag ctagggcgct gctaggcagc tggctcgctt ttccnaagaa acaacgctcc 600
taattaattt ggttggaggg gcaaatcttg tcttgtcagc agctaacgca cacgtgatgt 660
gtgtgtgtgt acggtgtgcc cctaccggac cccnnnttgg ccanctacnn cnctcgnncc 720
ttta 724

<210> SEQ ID NO 148
<211> LENGTH: 719
<212> TYPE: DNA
<213> ORGANISM: Artificial sequence
<220> FEATURE:
<223> OTHER INFORMATION: PH467
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:

<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t

<400> SEQUENCE: 148
nnnnnnnnnn nnnnnnnnnn tcgttgcgcc ngcaccanna ccngcaccac cngaaccaga 60
gaacgacgac nagtcgacga ccattccccg ccgtacgacg cccacgtggt accgccttcg 120
ccgctagctc cggccggccg ggaagcagtc gtcgcggccg ccacgtagag ggacggacca 180
cccttcgaat aatagttagc ccgggacttg gcacgttcta gttggaacag agacaacgga 240
gccagacgta cggatcttga atccacaaga gagcaaaact ctctctctgt atccatctca 300
tgcaatggtt ttagttaggc cctgtttcaa tctcatggga taaagtttag cttcctgcta 360
aactttagct atatgaattg aagtgctaaa gtttagcttc aattaccacc attagctctc 420
ctgtttagat tacaaatggc taaaagtagc taaaaaatag ctgctaaagt ttatctcgcg 480
agattgaaac aggcccttag ctcagttgat gagttttttt tagttagctc cnaatccttg 540
ctgactgcta gctagggcgc tgctaggcag ctggctcgct tttccnaaga aacaacgctc 600
ctaattaatt tggttggagg ggcaaatctt gtcttgtcag cagctaacgc acacntgatg 660
tgtgtgtgtg tgtacggtgt gcccctacng ganccncagc ttggccanct acctcnctc 719

<210> SEQ ID NO 149
<211> LENGTH: 725
<212> TYPE: DNA
<213> ORGANISM: Artificial sequence
<220> FEATURE:
<223> OTHER INFORMATION: PH48F
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t

<400> SEQUENCE: 149

```
nnnnnnnnnn nnnnnnnnnn cnttgcgccn gcaccngcac cngcaccncc ngaaccagag     60

aacgacgacg agtcgacgac cattccccgc cgtacgacgc ccacgtagta ccgccttcgc    120

cgctagctcc ggccggccgg aagcagtcgt cgcggccgcc acgtagaggg acggaccacc    180

cttcgaataa tagttagccc gggacttggc acgttctaga tggaacagag acaacggagc    240

cagacgtacg gatcttgaat ccacaagaga gcaaaactct ctctctgtat ccntctcatg    300

caatggtttt agttaggccc tgtttcaatc tcatgggata aagtttagct tcctgctaaa    360

ctttagctat atgaattgaa gtgctaaagt ttagcttcaa ttaccaccat tagctctcct    420

gtttagatta caaatggcta aaagtagcta aaaaatagct gctaaagttt atctcgcgag    480

attgaaacag gcccttagct cagttgatga gtttttttta gttagctccn aatccttgct    540

gactgctagc tagggcgctg ctaggcagct ggctcgcttt tccnaagaaa caacgctcct    600

aattaatttg gttggagggg caaatcttgt cttgtcagca gctaacgcac acgtgatgtg    660

tgtgtgtgta cggtgtgccc ctaccggacc ccancttggc cagctacctc gctcncncct    720

ttacn                                                                 725
```

<210> SEQ ID NO 150
<211> LENGTH: 745
<212> TYPE: DNA
<213> ORGANISM: Artificial sequence
<220> FEATURE:
<223> OTHER INFORMATION: PH7WC
<220> FEATURE:

<221> NAME/KEY: misc_feature
<222> LOCATION: (1)..(26)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(47)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t

```
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (741)..(745)
<223> OTHER INFORMATION: n is a, c, g, or t

<400> SEQUENCE: 150

nnnnnnnnnn nnnnnnnnnn nnnnnntgcg cnngcaccng caccnnncac cnccngaacc      60

ngagaacgac gacgagtcga cgaccattcc ccgccgtacg acgcccacgt ggtaccgcct     120

tcgccgctng ctccggccgg ccgggaagca gtcgtcgcgg ccgccacgta gagggacgga     180

ccacccttcg aataatagtt agcccgggac ttggcacgtt ctagttggaa cagagacnac     240

ggagccagac gtacggatct tgaatccaca agagagcaaa actctctctc tgtatccatc     300

tcatgcaatg gttttagtta ggccctgttt caatctcatg ggataaagtt tagcttcctg     360

ctaaacttta gctatatgaa ttgaagtgct aaagtttagc ttcaattacc accattagct     420

ctcctgttta gattacaaat ggctaaaagt agctaaaaaa tagctgctaa agtttatctc     480

gcgagattga aacaggccct tagctcagtt gatgagtttt ttttagttag ctccnaatcc     540

ttgctgactg ctagctaggg cgctgctagg cngctggctc gcttttccna agaaacaacg     600

ctcctaatta atttggttgg aggggcaaat cttgtcttgt cngcngctaa cgcacacgtg     660

atgtgtgtgt gtgtacngtg tgcccctacc gganccccagc ttggccngct acctcgctcn     720

cgccnttacc anctanccna nnnnn                                           745


<210> SEQ ID NO 151
<211> LENGTH: 682
<212> TYPE: DNA
<213> ORGANISM: Artificial sequence
<220> FEATURE:
<223> OTHER INFORMATION: 625
<220> FEATURE:
<221> NAME/KEY: misc_feature
<222> LOCATION: (1)..(23)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (587)..(587)
```

<223> OTHER INFORMATION: n is a, c, g, or t
<220> FEATURE:
<221> NAME/KEY: misc_feature
<222> LOCATION: (681)..(682)
<223> OTHER INFORMATION: n is a, c, g, or t

<400> SEQUENCE: 151

```
nnnnnnnnnn nnnnnnnnnn nnncgttgcg ccngcaccng cacnngcacc accngaacca     60

gagaacgacg acnagtcgac gaccattccc cgccgtacga cgcccacgta gtaccgcctt    120

cgccgctagc tccggccggc cggaagcagt cgtcgcggcc gccacgtaga gggacggacc    180

acccttcgaa taatagttag cccgggactt ggcacgttct agatggaaca gagacaacgg    240

agccagacgt acggatcttg aatccacaag agagcaaaac tctctctctg tatccatctc    300

atgcaatggt tttagttagg ccctgtttca atctcatggg ataaagttta gcttcctgct    360

aaactttagc tatatgaatt gaagtgctaa agtttagctt caattaccac cattagctct    420

cctgtttaga ttacaaatgg ctaaaagtag ctaaaaaata gctgctaaag tttatctcgc    480

gagattgaaa caggccctta gctcagttga tgagtttttt ttagttagct ccnaatcctt    540

gctgactgct agctagggcg ctgctaggca gctggctcgc ttttccnaag aaacaacgct    600

cctaattaat ttggttggag gggcaaatct tgtcttgtca gcagctaacg cacacgtgat    660

gtgtgtgtgt gtacggtgtg nn                                             682
```

<210> SEQ ID NO 152
<211> LENGTH: 677
<212> TYPE: DNA
<213> ORGANISM: Artificial sequence
<220> FEATURE:
<223> OTHER INFORMATION: PHP3P1
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t

<400> SEQUENCE: 152

```
nnnnnnnnnn nnnnnnnnnn ntcgttgcgc cngcaccngc accngcacca ccngaaccng     60

agaacgacga cgagtcgacg accattcccc gccgtacgac gccnacgtgg taccgccttc    120

gccgctagct ccggccggcc gggaagcagt cgtcgcggcc gccacgtaga gggacggacc    180

acccttcgaa taatagttag cccgggactt ggcacgttct agttggaaca gagacaacgg    240

agccagcaga cgtacggatc ttgaatccac aagagagcaa aactctctct ctgtatccat    300

ctcatgcaat ggttttagtt aggccctgtt tcaatctcat gggataaagt ttagcttcct    360

gctaaacttt agctatatga attgaagtgc taaagtttag cttcaattac caccattagc    420

tctcctgttt agattacaaa tggctaaaag tagctaaaaa atagctgcta aagtttatct    480

cgcgagattg aaacaggccc ttagctcagt tgatgagttt tttttagtta gctccaaatc    540

cttgctgact gctagctagg gcgctgctag gcagctggct cgcttttccn aagaaacaac    600

gctcctaatt aatttggttg gaggggcnaa tcttgtcttg tcancagcta acgcacacgt    660

gatgtgtgtg tgtgtac                                                   677
```

<210> SEQ ID NO 153
<211> LENGTH: 680
<212> TYPE: DNA
<213> ORGANISM: Artificial sequence
<220> FEATURE:
<223> OTHER INFORMATION: PHY7M2
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:

<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (655)..(656)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (679)..(680)
<223> OTHER INFORMATION: n is a, c, g, or t

<400> SEQUENCE: 153
nnnnnnnnnn nnnnnnntnn ttnnntgcgc cngcaccngc accngcacca ccngaaccag 60
agaacgacga cgagtcgacg accattcccc gccgtacgac gccnacgtgg taccgccttc 120
gccgctagct ccggccggcc ggaagcagtc gtcgcggccg ccacgtagag ggacggacca 180
cccttcgaat aatagttagc ccgggacttg gcacgttcta gatggaacag agacaacgga 240
gccagacgta cggatcttga atccacaaga gagcaaaact ctctctctgt atccatctca 300
tgcaatggtt ttagttaggc cctgtttcaa tctcatggga taaagtttag cttcctgcta 360
aactttagct atatgaattg aagtgctaaa gtttagcttc aattaccacc attagctctc 420
ctgtttagat tacaaatggc taaaagtagc taaaaaatag ctgctaaagt ttatctcgcg 480
agattgaaac aggcccttan ctcanttgat gagttttttt tagtaanctc cnaatccttg 540
ctgactgcta gctagggcgc tgctaggcag ctggctcgct tttccnaaga aacaacgctc 600
cnaattaatt tggttggagg ggcaaatctt gtcntgtcag canctaangc acacnngatg 660
tgtgtgtgtg tacggngtnn 680

<210> SEQ ID NO 154
<211> LENGTH: 730
<212> TYPE: DNA
<213> ORGANISM: Artificial sequence
<220> FEATURE:
<223> OTHER INFORMATION: PH147G5
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t

<400> SEQUENCE: 154
nnnnnnnnnn nnnnnnnnnn tcgttgcgcc ngcaccngca ccngcaccac cngaaccnga 60
gaacgacgac gagtcgacga ccattccccg ccgtacgacg cccacgtggt accgccttcg 120
ccgctagctc cggccggccg ggaagcagtc gtcgcggccg ccacgtagag ggacggacca 180
cccttcgaat aatagttagc ccgggacttg gcacgttcta gttggaacag agacaacgga 240
gccagcagac gtacggatct tgaatccaca agagagcaaa actctctctc tgtatccatc 300
tcatgcaatg gttttagtta ggccctgttt caatctcatg ggataaagtt tagcttcctg 360
ctaaacttta gctatatgaa ttgaagtgct aaagtttagc ttcaattacc accattagct 420
ctcctgttta gattacaaat ggctaaaagt agctaaaaaa tagctgctaa agtttatctc 480
gcgagattga aacaggccct tagctcagtt gatgagtttt ttttagttag ctccnaatcc 540
ttgctgactg ctagctaggg cgctgctagg cagctggctc gcttttccna agaaacaacg 600
ctcctaatta atttggttgg aggggcaaat cttgtcttgt cagcngctaa cgcacacgtg 660
atgtgtgtgt gtgtacggtg tgcccctacc ggaccccagc ttggcnnnct acctcgctcg 720 cgccnttacn 730

<210> SEQ ID NO 155
<211> LENGTH: 21
<212> TYPE: DNA
<213> ORGANISM: Artificial sequence
<220> FEATURE:
<223> OTHER INFORMATION: PHMTR

<400> SEQUENCE: 155
ttgatgagtt tttttagtt a 21

<210> SEQ ID NO 156
<211> LENGTH: 20
<212> TYPE: DNA
<213> ORGANISM: Artificial sequence
<220> FEATURE:
<223> OTHER INFORMATION: PHMTR-T

<400> SEQUENCE: 156
ttgatgagtt tttttagtta 20

<210> SEQ ID NO 157
<211> LENGTH: 25
<212> TYPE: DNA
<213> ORGANISM: Artificial
<220> FEATURE:
<223> OTHER INFORMATION: C06621-1-K2 R primer for Marker 1

<400> SEQUENCE: 157
ttacggccac ctctgtgtgt cattt 25

<210> SEQ ID NO 158
<211> LENGTH: 26
<212> TYPE: DNA
<213> ORGANISM: Artificial
<220> FEATURE:
<223> OTHER INFORMATION: C06621-1-K2 R primer for Marker 2

<400> SEQUENCE: 158
gcggttttca atcaatggga agccta 26

<210> SEQ ID NO 159
<211> LENGTH: 45
<212> TYPE: DNA
<213> ORGANISM: Artificial
<220> FEATURE:
<223> OTHER INFORMATION: C06621-1-K2 F primer for Marker 1 + VIC

<400> SEQUENCE: 159
gaaggtcgga gtcaacggat tcctccacgc tgaacttaac ctgag 45

<210> SEQ ID NO 160
<211> LENGTH: 45
<212> TYPE: DNA
<213> ORGANISM: Artificial
<220> FEATURE:
<223> OTHER INFORMATION: C06621-1-K2 F primer for Marker 2 + FAM

<400> SEQUENCE: 160
gaaggtgacc aagttcatgc tgtggaagtc ccaacaaagt ggtag 45

<210> SEQ ID NO 161
<211> LENGTH: 25
<212> TYPE: DNA
<213> ORGANISM: Artificial
<220> FEATURE:
<223> OTHER INFORMATION: C06621-1-K4 R primer for Marker 1

<400> SEQUENCE: 161
ttacggccac ctctgtgtgt cattt 25

<210> SEQ ID NO 162
<211> LENGTH: 26
<212> TYPE: DNA
<213> ORGANISM: Artificial
<220> FEATURE:
<223> OTHER INFORMATION: C06621-1-K4 R primer for Marker 2

<400> SEQUENCE: 162
gcggttttca atcaatggga agccta 26

<210> SEQ ID NO 163
<211> LENGTH: 44
<212> TYPE: DNA
<213> ORGANISM: artificial
<220> FEATURE:
<223> OTHER INFORMATION: C06621-1-K4 F primer for Marker 1 + VIC

<400> SEQUENCE: 163
gaaggtcgga gtcaacggat tctccacgct gaacttaacc tgag 44

<210> SEQ ID NO 164
<211> LENGTH: 45
<212> TYPE: DNA
<213> ORGANISM: artificial
<220> FEATURE:
<223> OTHER INFORMATION: C06621-1-K4 F primer for Marker 2 + FAM

<400> SEQUENCE: 164
gaaggtgacc aagttcatgc tgtggaagtc ccaacaaagt ggtag 45

<210> SEQ ID NO 165
<211> LENGTH: 21
<212> TYPE: DNA
<213> ORGANISM: artificial
<220> FEATURE:
<223> OTHER INFORMATION: SEQ ID NO:165 FAM

<400> SEQUENCE: 165
gaaggtgacc aagttcatgc t 21

<210> SEQ ID NO 166
<211> LENGTH: 21
<212> TYPE: DNA
<213> ORGANISM: artificial
<220> FEATURE:
<223> OTHER INFORMATION: SEQ ID NO:166 VIC

<400> SEQUENCE: 166
gaaggtcgga gtcaacggat t 21

<210> SEQ ID NO 167
<211> LENGTH: 607
<212> TYPE: DNA
<213> ORGANISM: artificial
<220> FEATURE:
<223> OTHER INFORMATION: SEQ ID NO:167 Ct9050b191E02m reference sequence

<400> SEQUENCE: 167
acccacaaaa ctatcagtgt gctaagcact gcatagagca tgacccactg atagcctcat 60
aggtacatga tcacagaagc atgcactcat tagatttgaa gtgacagctt aaaatgcatt 120
gctgtgccag gaaattgttt gcaacatacc caacctcgtt gtcatataaa ggaaccaata 180
atgcgtttcg aaatttcata tgggtgtgct cgtccacgtg tttgcagcca ttttgcgcag 240
aaagtgatac cttaacacgt ttggcgtact cctgtagcgt ggattggtag cactcgtgaa 300
tgatggaagt aggcacctcc acgctgaact taacctgcga agaaatgaca cacagaggtg 360
gccgtaaaaa atcaaagcga gacaaaggaa ggggaggccg gaggtggcgg gggctcacac 420
tggatccagg ctgcggcgtc ttggtgacac ggagcgagtc tccgccccg gcagtggcct 480

-continued

```
cgcggagctc cacggcggcc gaggtgacgg ggagccagcg cagccgccgt cgcgaggacg    540

tggaggagag acagcgggag gtgtaggcga gcgagagact ggtccacgag acggaggcag    600

aagactg                                                              607
```

GENETIC LOCI ASSOCIATED WITH RESISTANCE TO TROPICAL RUST IN MAIZE

CROSS-REFERENCE TO RELATED APPLICATION

This application claims the benefit of U.S. Provisional Application No. 61/257,977, filed Nov. 4, 2009, which is incorporated by reference in its entirety.

FIELD OF THE INVENTION

The present disclosure relates to compositions and methods useful in enhancing resistance to tropical rust in plants and methods to identify allelic variations associated with a trait of interest.

BACKGROUND OF THE INVENTION

Tropical rust is a fungal disease caused by the pathogen *Physopella zeae* (Mains) Cummins & Ramachar (syn. *Angiopsora zeae* Mains), previously classified as *Angiopsora zeae* Mains (Donald G. White, ed. 1999. Compendium of corn diseases. Third edition. APS Press, ISBN 0-89054-234-1). Tropical rust can spread very rapidly, killing the plant in a short time.

Disease management strategies include crop rotation, destruction of old maize residues by tillage, and fungicide application, all of which are aimed at reducing the fungal inoculum. However, the most effective and most preferred method of control for tropical rust is the planting of resistant hybrids.

The methods of controlling tropical rust by reducing fungal inoculum require additional time and resources on the part of the farmer, and in addition, can have detrimental effects on the environment. This makes the planting of resistant hybrids even more attractive to farmers and the general public. Thus, it is desirable to provide compositions and methods for identifying and selecting maize plants with enhanced resistance to tropical rust.

SUMMARY OF THE INVENTION

Compositions and methods for identifying and selecting maize plants with enhanced resistance to tropical rust are provided. Also provided are methods for marker assisted selection of plants that have enhanced resistance to tropical rust.

In one embodiment, methods for selecting maize plants or germplasm with enhanced resistance to tropical rust by detecting the presence of at least one allele of a first marker locus that is linked to and associated with the "T" deletion at position 16 of PHMTR (SEQ ID NO:155) or the "GAG" haplotype at positions 337-339 of reference sequence SEQ ID NO:167 and selecting the maize plants or germplasm that comprise the at least one allele of a first marker locus that is linked to and associated with the "T" deletion at position 16 of PHMTR (SEQ ID NO:155) or the "GAG" haplotype at positions 337-339 of reference sequence SEQ ID NO:167 are provided. The at least one allele of the first marker locus can be linked to and associated with the "T" deletion at position 16 of PHMTR (SEQ ID NO:155) or the "GAG" haplotype at positions 337-339 of reference sequence SEQ ID NO:167 by up to 20 cM on a single meiosis map.

In another embodiment, methods for selecting maize plants or germplasm with enhanced resistance to tropical rust by detecting the "T" deletion at position 16 of PHMTR (SEQ ID NO:155) or the "GAG" haplotype at positions 337-339 of reference sequence SEQ ID NO:167; and selecting the maize plants or germplasm that comprise the "T" deletion at position 16 of PHMTR (SEQ ID NO:155) or the "GAG" haplotype at positions 337-339 of reference sequence SEQ ID NO:167 are provided.

In another embodiment, methods for identifying maize plants with enhanced resistance to tropical rust by detecting a marker locus in the genome of the maize plant using the sequence of the marker locus, a portion of the sequence of the marker locus, or a complement of the sequence of the marker locus, or of a portion thereof, as a marker probe, are provided. The marker probe hybridizes under stringent conditions to the contiguous DNA between and including SEQ ID NO:89, or a nucleotide sequence that is 95% identical to SEQ ID NO:89 based on the Clustal V method of alignment, and SEQ ID NO:96, or a nucleotide sequence that is 95% identical to SEQ ID NO:96 based on the Clustal V method of alignment, and the marker locus comprises at least one allele that is associated with the enhanced resistance to tropical rust.

In another embodiment, methods for identifying maize plants with enhanced resistance to tropical rust by detecting at least one marker allele associated with the enhanced resistance in the germplasm of the maize plant are provided. The marker locus can be selected from any of the following marker loci: PHM1192-26-U, PHM1192-4-U, C00435-802-U, C00436-801-U, PHM187-7-U, C00423-801-U, PHM5028-24-U, PHM13818-15-U, PHM15721-39-U, PHM15721-180-U, C00441-801-U, C00441-802-U, PHM4370-19-U, PHM731-107-U, C00071-01-U, PHM8249-21-U, C00428-801-U, PHM18427-13-U, PHM9535-10-U, PHM9535-6-U, PHM9535-7-U, and PHM4003-13-U; the PHM markers PHM15590, PHM13818, PHM1192, PHM187, PHM5028, PHM4370, PHM731, and PHM15721; Sub2e, Sub9d, Sub19c, Sub23m, C06621-1-K2, and C06621-1-K4; as well as any other marker that is linked to these markers. The marker locus can also be found within any of the following intervals on chromosome 10 comprising and flanked by:

i. PHM15590 and PHM9535;

ii. PHM15590 and PHM15721;

iii. C00441 and C00428;

iv. PHM731 and PHM15721; and v. C00071 and PHM731.

The marker locus comprises at least one allele that is associated with enhanced resistance to tropical rust.

In another embodiment, methods for identifying maize plants with enhanced resistance to tropical rust by detecting a haplotype in the germplasm of the maize plant that is associated with enhanced resistance to tropical rust are provided. The haplotype comprises alleles at one or more marker loci, wherein the one or more marker loci are found within any of the following intervals on chromosome 10 comprising and flanked by:

i. PHM15590 and PHM9535;

ii. PHM15590 and PHM15721;

iii. C00441 and C00428;

iv. PHM731 and PHM15721; and v. C00071 and PHM731.

The haplotype can comprise a "T" deletion at position 16 of PHMTR or "GAG" at positions at 337-339 of reference sequence SEQ ID NO:167.

In another embodiment, methods of selecting maize plants with enhanced resistance to tropical rust are provided. In this method, a first maize plant is obtained wherein the maize plant has at least one allele of a marker locus that is located within any of the following intervals on chromosome 10 comprising and flanked by:

i. PHM15590 and PHM9535;

ii. PHM15590 and PHM15721;

iii. C00441 and C00428;

iv. PHM731 and PHM15721; and v. C00071 and PHM731;

and the allele is associated with enhanced resistance to tropical rust. The first maize plant is crossed to a second maize plant, and the resulting progeny plants are evaluated for the allele of the first maize plant. Progeny plants that possess the allele of the first maize plant are then selected as having enhanced resistance to tropical rust.

In another embodiment, methods of selecting maize plants with enhanced resistance to tropical rust are provided. In this method, a first maize plant is obtained wherein the maize plant comprises in its genome the "T" deletion at position 16 of PHMTR or the "GAG" haplotype at positions 337-339 of reference sequence SEQ ID NO:167. The first maize plant is crossed to a second maize plant, and the resulting progeny plants are evaluated for the "T" deletion at position 16 of PHMTR or the "GAG" haplotype at positions 337-339 of reference sequence SEQ ID NO:167. Progeny plants that possess the "T" deletion at position 16 of PHMTR or the "GAG" haplotype at positions 337-339 of reference sequence SEQ ID NO:167 are then selected as having enhanced resistance to tropical rust.

Additionally, maize plants identified or selected by the methods described above, wherein the plant is not CML339, are of interest. Furthermore, progeny of maize plants identified or selected by the methods described above are of interest.

In another embodiment, methods of identifying allelic variations associated with a desirable form of a trait are presented. In these methods, raw sequences are aligned with an open:extension cost ratio greater than 10 and background noise is removed by trimming the tails. Random allelic variation is then trimmed, and an unweighted pair group method with arithmetic mean (UPGMA) is applied. The trimming of random allelic variation and the application of UPGMA to the alignment are repeated until a phenogram is identified. Allelic variations associated with the phenotype of interest can then be identified from the phenogram.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the physical map arrangement of sequenced BACs (obtained from the Maize Genome Browser, which is publicly available on the internet) that assemble to the chromosome 10 region defined by and including BACs c0497L12 and b0191E02. The positions of the PHM markers described herein (region defined by and including PHM15590 and PHM15721) are indicated, as are the positions of the public markers lying within the interval.

FIGS. 2A and 2B show the frequency distributions of PH468×PHS6Y F2 population for tropical and southern rust scores, respectively.

FIG. 3 shows the composite interval mapping results obtained using the PH468×PHS6Y F2 population. A peak of significance was identified on the short arm of chromosome 10. Marker positions on the x-axis correspond to the PHB genetic map. The y-axis represents the LOD score.

FIG. 4 (*a*) Susceptible inbred line and corresponding resistant conversion using PHS6Y as donor parent. (*b*) Hybrid made with a susceptible version of an inbred. (*c*) Hybrid made with the resistant ("converted") version of the same inbred. This shows that the tropical rust gene has a dominant effect in the hybrid level.

FIG. 5 shows a hybrid that is highly susceptible to tropical rust (on left) and the same hybrid that has been converted to have enhanced resistance from PHS6Y (on right).

Figure 1:
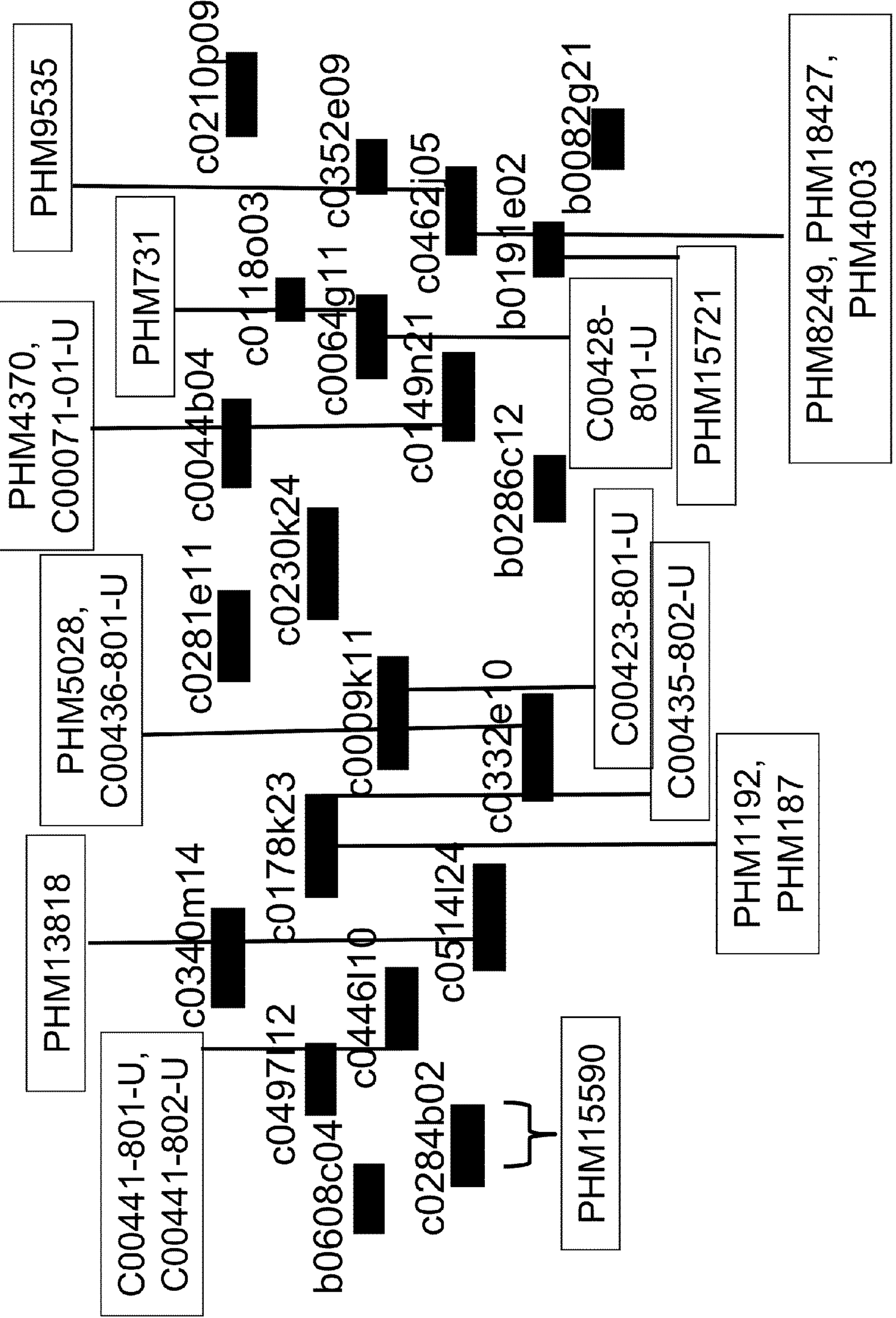

FIG. 7 shows part of the reference sequence (top) obtained by the genotyping of maize lines resistant and susceptible to tropical rust using PCR primers (SEQ ID NOs: 133 and 134) designed for clone ID Ct9050c064G11c (Table 9). SEQ ID NOs:137-142 represent amplicons obtained from resistant lines, while SEQ ID NOs: 143-154 represent amplicons obtained from susceptible lines. The area highlighted in grey represents a 21 bp-region of the reference sequence (referred to as PHMTR; SEQ ID NO:155). Maize lines having a T-deletion at by 16 (indicated by the arrow) all showed enhanced resistance to tropical rust and have the sequence of SEQ ID NO:156.

FIG. 8 shows part of the alignment of amplicon sequences obtained using primers SEQ ID NO:135 and SEQ ID NO:136. A "GAG" haplotype (boxed) was found to be unique to all lines with enhanced resistance to tropical rust.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists the sequences described herein that are associated with the InvaderPlus Production markers, along with the corresponding identifiers (SEQ ID NO:) as used in the attached Sequence Listing.

TABLE 1

| InvaderPlus Production Markers | | | | | | | | | |
|---|---|---|---|---|---|---|---|---|---|
| Marker Name | Forward Primer SEQ ID NO: | Reverse Primer SEQ ID NO: | Sense | Allele 1 | Allele 2 | Dye 1 | Dye 2 | Probe 1 SEQ ID NO: | Probe 2 SEQ ID NO: |
| PHM1192-26-U | 1 | 2 | ANTI-SENSE | G | A | FAM | RED | 3 | 4 |
| PHM1192-4-U | 5 | 6 | SENSE | D | I | FAM | RED | 7 | 8 |
| C00435-802-U | 9 | 10 | SENSE | A | T | RED | FAM | 11 | 12 |
| C00436-801-U | 13 | 14 | SENSE | A | G | RED | FAM | 15 | 16 |
| PHM187-7-U | 17 | 18 | ANTI-SENSE | G | A | FAM | RED | 19 | 20 |
| C00423-801-U | 21 | 22 | SENSE | T | C | RED | FAM | 23 | 24 |
| PHM5028-24-U | 25 | 26 | ANTI-SENSE | T | C | FAM | RED | 27 | 28 |
| PHM13818-15-U | 29 | 30 | SENSE | T | C | FAM | RED | 31 | 32 |
| PHM15721-39-U | 33 | 34 | ANTI-SENSE | D | I | FAM | RED | 35 | 36 |
| PHM15721-180-U | 37 | 38 | SENSE | C | T | FAM | RED | 39 | 40 |
| C00441-801-U | 41 | 42 | SENSE | T | G | RED | FAM | 43 | 44 |
| C00441-802-U | 45 | 46 | SENSE | T | C | RED | FAM | 47 | 48 |
| PHM4370-19-U | 49 | 50 | SENSE | G | A | FAM | RED | 51 | 52 |
| PHM731-107-U | 53 | 54 | SENSE | T | C | FAM | RED | 55 | 56 |
| C00071-01-U | 57 | 58 | ANTI-SENSE | D | I | FAM | RED | 59 | 60 |
| PHM8249-21-U | 61 | 62 | SENSE | T | C | FAM | RED | 63 | 64 |
| C00428-801-U | 65 | 66 | ANTI-SENSE | G | A | RED | FAM | 67 | 68 |
| PHM18427-13-U | 69 | 70 | ANTI-SENSE | D | I | FAM | RED | 71 | 72 |
| PHM9535-10-U | 73 | 74 | SENSE | G | T | FAM | RED | 75 | 76 |
| PHM9535-6-U | 77 | 78 | ANTI-SENSE | T | A | FAM | RED | 79 | 80 |
| PHM9535-7-U | 81 | 82 | ANTI-SENSE | G | A | FAM | RED | 83 | 84 |
| PHM4003-13-U | 85 | 86 | ANTI-SENSE | T | C | FAM | RED | 87 | 88 |

Table 2 lists the sequences described herein that are associated with the PHM markers, along with the corresponding identifiers (SEQ ID NO:) as used in the attached Sequence Listing.

TABLE 2

| PHM Marker Sequences: amplicon and primer information | | | | |
|---|---|---|---|---|
| Marker Locus | Amplicon reference sequence (SEQ ID NO:) | Primer | Forward Primer (SEQ ID NO:) | Reverse Primer (SEQ ID NO:) |
| PHM15590 | 89 | Internal | 98 | 99 |
| | | External | 97 | 100 |
| PHM13818 | 90 | Internal | 102 | 103 |
| | | External | 101 | 104 |
| PHM1192 | 91 | Internal | 106 | 107 |
| | | External | 105 | 108 |
| PHM187 | 92 | Internal | 110 | 111 |
| | | External | 109 | 112 |
| PHM5028 | 93 | Internal | 114 | 115 |
| | | External | 113 | 116 |
| PHM4370 | 94 | Internal | 118 | 119 |
| | | External | 117 | 120 |
| PHM731 | 95 | Internal | 122 | 123 |
| | | External | 121 | 124 |
| PHM15721 | 96 | Internal | 126 | 127 |
| | | External | 125 | 128 |

SEQ ID NO:129 is the L primer designed for Clone ID Ct9050c497L12e.

SEQ ID NO:130 is the R primer designed for Clone ID Ct9050c497L12e.

SEQ ID NO:131 is the L primer designed for Clone ID Ct9050c064G11d.

SEQ ID NO:132 is the R primer designed for Clone ID Ct9050c064G11d.

SEQ ID NO:133 is the L primer designed for Clone ID Ct9050c064G11c.

SEQ ID NO:134 is the R primer designed for Clone ID Ct9050c064G11c.

SEQ ID NO:135 is the L primer designed for Clone ID Ct9050b191E02m.

SEQ ID NO:136 is the R primer designed for Clone ID Ct9050b191E02m.

SEQ ID NO:137 is the sequence of the amplicon obtained using SEQ ID NO:133 and SEQ ID NO:134 as the primers and PHS6Y DNA.

SEQ ID NO:138 is the sequence of the amplicon obtained using SEQ ID NO:133 and SEQ ID NO:134 as the primers and PH1JG22 DNA. PH1JG22 is a maize inbred line that is resistant to tropical rust.

SEQ ID NO:139 is the sequence of the amplicon obtained using SEQ ID NO:133 and SEQ ID NO:135 as the primers and PH1 FT71 DNA. PH1 FT71 is a maize inbred line that is resistant to tropical rust.

SEQ ID NO:140 is the sequence of the amplicon obtained using SEQ ID NO:133 and SEQ ID NO:135 as the primers and PH1G3H1 DNA. PH1G3H1 is a maize inbred line that is resistant to tropical rust.

SEQ ID NO:141 is the sequence of the amplicon obtained using SEQ ID NO:133 and SEQ ID NO:135 as the primers and PH1JG01 DNA. PH1JG01 is a maize inbred line that is resistant to tropical rust.

SEQ ID NO:142 is the sequence of the amplicon obtained using SEQ ID NO:133 and SEQ ID NO:135 as the primers and PHS7W DNA. PHS7W is a maize inbred line that is resistant to tropical rust.

SEQ ID NO:143 is the sequence of the amplicon obtained using SEQ ID NO:133 and SEQ ID NO:135 as the primers and PH7W3 DNA. PH7W3 is a maize inbred line that is susceptible to tropical rust.

SEQ ID NO:144 is the sequence of the amplicon obtained using SEQ ID NO:133 and SEQ ID NO:135 as the primers and PH9VF DNA. PH9VF is a maize inbred line that is susceptible to tropical rust.

SEQ ID NO:145 is the sequence of the amplicon obtained using SEQ ID NO:133 and SEQ ID NO:135 as the primers and PHBNA DNA. PHBNA is a maize inbred line that is susceptible to tropical rust.

SEQ ID NO:146 is the sequence of the amplicon obtained using SEQ ID NO:133 and SEQ ID NO:135 as the primers and PH2JR DNA. PH2JR is a maize inbred line that is susceptible to tropical rust.

SEQ ID NO:147 is the sequence of the amplicon obtained using SEQ ID NO:133 and SEQ ID NO:135 as the primers and PH0TJ DNA. PH0TJ is a maize inbred line that is susceptible to tropical rust.

SEQ ID NO:148 is the sequence of the amplicon obtained using SEQ ID NO:133 and SEQ ID NO:135 as the primers and PH467 DNA. PH467 is a maize inbred line that is susceptible to tropical rust.

SEQ ID NO:149 is the sequence of the amplicon obtained using SEQ ID NO:133 and SEQ ID NO:135 as the primers and PH48F DNA. PH48F is a maize inbred line that is susceptible to tropical rust.

SEQ ID NO:150 is the sequence of the amplicon obtained using SEQ ID NO:133 and SEQ ID NO:135 as the primers and PH7WC DNA. PH7WC is a maize inbred line that is susceptible to tropical rust.

SEQ ID NO:151 is the sequence of the amplicon obtained using SEQ ID NO:133 and SEQ ID NO:135 as the primers and 625 DNA. 625 is a maize inbred line that is susceptible to tropical rust.

SEQ ID NO:152 is the sequence of the amplicon obtained using SEQ ID NO:133 and SEQ ID NO:135 as the primers and PHP3P1 DNA. PHP3P1 is a maize inbred line that is susceptible to tropical rust.

SEQ ID NO:153 is the sequence of the amplicon obtained using SEQ ID NO:133 and SEQ ID NO:135 as the primers and PHY7M2 DNA. PHY7M2 is a maize inbred line that is susceptible to tropical rust.

SEQ ID NO:154 is the sequence of the amplicon obtained using SEQ ID NO:133 and SEQ ID NO:135 as the primers and PH147G5 DNA. PH147G5 is a maize inbred line that is susceptible to tropical rust.

SEQ ID NO:155 is the sequence of the PHMTR region.

SEQ ID NO:156 is the sequence of the PHMTR region without the "T" at position 16 of SEQ ID NO:155.

SEQ ID NOs:157-164 are the sequences for primers C06621-1-K2 and C06621-1-K4 (Table 3).

TABLE 3

C06621-1-K2 and C06621-1-K4 KASP Marker Information

| Marker Name | C06621-1-K2 | C06621-1-K4 |
|---|---|---|
| Reverse Primer for Marker 1 (Target Specific) | SEQ ID NO: 157 | SEQ ID NO: 161 |
| Reverse Primer for Marker 2 (Internal control) | SEQ ID NO: 158 | SEQ ID NO: 162 |
| Allele1 | P | P |
| Allele2 | X | X |
| Dye1 | VIC | VIC |
| Dye2 | FAM | FAM |

TABLE 3-continued

C06621-1-K2 and C06621-1-K4 KASP Marker Information

| Marker Name | C06621-1-K2 | C06621-1-K4 |
|---|---|---|
| Forward Primer for Marker 1 + VIC universal Sequence (Target Specific) | SEQ ID NO: 159 | SEQ ID NO: 163 |
| Forward Primer for Marker 2 + FAM universal Sequence (Internal Control) | SEQ ID NO: 160 | SEQ ID NO: 164 |

SEQ ID NO:165 is the FAM universal sequence.

SEQ ID NO:166 is the VIC universal sequence.

SEQ ID NO:167 is the reference sequence for Sub23M.

DETAILED DESCRIPTION

The present invention provides allelic compositions in maize and methods for identifying and for selecting maize plants with enhanced resistance to tropical rust. Also within the scope of this invention are allelic compositions and methods used to identify and to counter-select maize plants that have decreased resistance to tropical rust. The following definitions are provided as an aid to understand this invention.

The term "Enhanced resistance", "increased resistance" or "newly conferred resistance" are used interchangeable and refers to an increased level of resistance against a particular pathogen, a wide spectrum of pathogens, or an infection caused by the pathogen(s). An increased level of resistance against a particular fungal pathogen, such tropical rust, for example, constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like. Herein, plants of the invention are described as having "enhanced resistance" to tropical rust infection, as a result of specific alleles at the locus of the invention.

A maize plant that displays enhanced resistance to tropical rust is a plant that is less affected with respect to yield and/or survivability or other relevant agronomic measures, upon introduction of the causative agents of that disease. Resistance is a relative term, indicating that the infected plant produces better yield of maize than another, similarly treated, more susceptible plant. That is, the conditions cause a reduced decrease in maize survival and/or yield in a resistant maize plant, as compared to a susceptible maize plant. One of skill will appreciate that maize plant resistance to tropical rust varies widely, can represent a spectrum of more resistant or less resistant phenotypes, and can vary depending on the severity of the infection. However, by simple observation, one of skill can determine the relative resistance or susceptibility of different plants, plant lines or plant families to tropical rust, and furthermore, will also recognize the phenotypic gradations of "resistant". As used in the art, "resistance" is sometimes referred to as "general resistance", "rate-reducing resistance", or "partial resistance".

"Disease resistance" is a characteristic of a plant, wherein the plant avoids the disease symptoms that are the outcome of plant-pathogen interactions, such as maize-tropical rust interactions. That is, pathogens are prevented from causing plant diseases and the associated disease symptoms, or alternatively, the disease symptoms caused by the pathogen are minimized or lessened. One of skill in the art will appreciate that the compositions and methods disclosed herein can be used with other compositions and methods available in the art for protecting plants from pathogen attack.

As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen.

A plant referred to herein as "diploid" has two sets of chromosomes.

A plant referred to herein as a "doubled haploid" is developed by doubling the haploid set of chromosomes. A doubled haploid plant is considered a homozygous plant.

An "elite line" is any line that has resulted from breeding and selection for superior agronomic performance.

The term "allele" refers to one of two or more different nucleotide sequences that occur at a specific locus.

"Allele frequency" refers to the frequency (proportion or percentage) of an allele within a population, or a population of lines. One can estimate the allele frequency within a population by averaging the allele frequencies of a sample of individuals from that population.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of a trait, and the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or 'contiguous DNA").

"Backcrossing" refers to the process whereby hybrid progeny are repeatedly crossed back to one of the parents. The "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unit during cell division and therefore can be said to be linked. can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

In bioinformatics, "clustering" refers to the grouping of sequences that are somehow related and is often used to make a non-redundant set of representative sequences. The sequences can be genomic, "transcriptomic" (ESTs) or protein in nature.

The term "complement" refers to a nucleotide sequence that is complementary to a given nucleotide sequence, i.e. the sequences are related by the base-pairing rules.

The term "contiguous DNA" refers to an uninterrupted stretch of genomic DNA represented by partially overlapping pieces or contigs.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

An "elite line" is any line that has resulted from breeding and selection for superior agronomic performance.

An "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus that confers, or contributes to, an agronomically desirable phenotype, e.g., enhanced resistance to tropical rust, and that allows the identification of plants that agronomically desirable phenotype. A "favorable" allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (i.e. their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

The term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, *Trends in Genetics* 9:275-280), Amplified Fragment Length Polymorphism (AFLP) (Vos et al, 1995, *Nucleic Acids Res.* 23:4407-4414), Single Nucleotide Polymorphism (SNP) (Brookes, 1999, *Gene* 234:177-186), Sequence Characterized Amplified Region (SCAR) (Paran and Michelmore, 1993, *Theor. Appl. Genet.* 85:985-993), Sequence Tagged Site (STS) (Onozaki et al., 2004, *Euphytica* 138:255-262), Single Stranded Conformation Polymorphism (SSCP) (Orita et al., 1989, *Proc Natl Acad Sci USA* 86:2766-2770), Inter-Simple Sequence Repeat (ISSR) (Blair et al., 1999, *Theor. Appl. Genet.* 98:780-792), Inter-Retrotransposon Amplified Polymorphism (IRAP), Retrotransposon-Microsatellite Amplified Polymorphism (REMAP) (Kalendar et al., 1999, *Theor. Appl. Genet.* 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to a series of polymorphisms with a specific sequence, such as a marker locus, or a series of polymorphisms across multiple sequences, e.g. multiple marker loci.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" refers to any of following maps: IBM, IBM2, IBM2 neighbors, IBM2 FPC0507, IBM2 2004 neighbors, IBM2 2005 neighbors, or IBM2 2005 neighbors frame. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps.

The term "inbred" refers to a line that has been bred for genetic homogeneity.

The term "indel" refers to an insertion or deletion, wherein one line may be referred to as having an insertion relative to a second line, or the second line may be referred to as having a deletion relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) *Marker-assisted Selection in Backcross Breeding*, Analysis of Molecular Marker Data, pp. 41-43. The initial cross gives rise to the F1 generation; the term "BC1" then refers to the second use of the recurrent parent, "BC2" refers to the third use of the recurrent parent, and so on.

As used herein, the term "linkage" is used to describe the degree with which one marker locus is associated with another marker locus or some other locus (for example, a tropical rust locus). The linkage relationship between a molecular marker and a phenotype (for example, enhanced resistance to tropical rust) is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a phenotype. A marker locus can be "associated with" (linked to) a trait, e.g., resistance to tropical rust. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker is located.

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zea mays* L. ssp. *mays* and is also known as corn.

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a gene or QTL, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus. Nucleic acids are "complementary" when they specifically "hybridize", or pair, in solution, e.g., according to Watson-Crick base pairing rules.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

"Tropical rust" is the disease caused by the pathogen *Physopella zeae* (Mains) Cummins & Ramachar (syn. *Angiopsora zeae* Mains). The disease is characterized by the formation of small round yellow pustules on the upper surface of the corn leaf. These uredial pustules are often found in small groups and the leaf epidermal layer covers the developing urediniospores. The obovoid to ellipsoid shaped urediniospores are released through a small slit or pore that forms in the epidermal layer. While the urediniospores are nearly colorless their released urediniospores give the pustules a white or creamy appearance. Some maize genotypes display pustules with a darker coloration (reddish to purplish) which accentuates the white/creamy urediniospores vs. a more traditional. A telial stage, with blister like appearance can also develop following uredial stage formation. The teliospores (brown to black in color) can develop within the telia which forms around the existing uredial pustules. (Donald G. White, ed. 1999. *Compendium of corn diseases*. Third edition. APS Press, ISBN 0-89054-234-1).

"Southern rust" is the disease caused by the pathogen *Puccinia polysora* Underw. The disease is characterized by small round yellow pustules that form primarily on the upper surface of the leaf, but occasionally break through to the lower leaf surface with uredial sporulation most often found adjacent to the leaf midrib. These uredial pustules contain the obovoid to ellipsoid shaped urediniospores, which typically are orange to reddish orange in coloration. The pustules often are round to oval in shape and become very numerous on the leaf. This pathogen can also form uredial pustules on the ear husk, ear shank and leaf sheaths. A telial stage is known to exist, with dark brown to black teliospores forming in telial which found in a semi-circle to circle around existing uredia.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A phenogram is a diagram depicting taxonomic relationships among organisms based on overall similarity of many characteristics without regard to evolutionary history or assumed significance of specific characters, usually generated by a computer.

The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

"Phylogenetic trees" are diagrams showing the inferred evolutionary relationships among various biological species or other entities based upon similarities and differences in their physical and/or genetic characteristics. They can be constructed using a variety of methods including but not limited to the distance-matrix methods such as neighbor-joining or UPGMA, which calculate genetic distance from multiple sequence alignments.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 ($p=0.05$, or a 5% probability) of random assortment is considered a significant indication of co-segregation. However, an acceptable probability can be any probability of less than 50% ($p=0.5$). For example, a significant probability can be less than 0.25, less than 0.20, less than 0.15, less than 0.1, less than 0.05, less than 0.01, or less than 0.001.

Each "PHM" marker represents two sets of primers (external and internal) that when used in a nested PCR, amplify a specific piece of DNA. The external set is used in the first round of PCR, after which the internal sequences are used for a second round of PCR on the products of the first round. This increases the specificity of the reaction. All of the PHM markers described herein are listed in Table 2, and the annealing temperature for these primers is 55° C.

A "production marker" or "production SNP marker" is a marker that has been developed for high-throughput purposes. Production SNP markers were developed for specific polymorphisms identified using PHM markers and the nested PCR analysis (see, for example, PHM1192-26-U in Table 1). The production SNP markers were designed for use with the Invader Plus® (Third Wave Technologies) platform.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment. Hence, a reference sequence identifies the polymorphisms in alleles at a locus. A reference sequence may not be a copy of an actual DNA sequence; however, it is useful for designing primers and probes for actual polymorphisms in the locus.

The term "progeny" refers to the offspring generated from a cross.

A "progeny plant" is generated from a cross between two plants.

The term "quantitative trait locus" or "QTL" refers to a region of DNA that is associated with the differential expression of a phenotypic trait in at least one genetic background, e.g., in at least one breeding population. QTLs are closely linked to the gene or genes that underlie the trait in question.

A "topcross test" is a progeny test derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

An "unfavorable allele" of a marker is a marker allele that segregates with the unfavorable plant phenotype, therefore providing the benefit of identifying plants that can be removed from a breeding program or planting.

Longer sequences hybridize specifically at higher temperatures. Generally, stringent conditions are selected to be about 3-5° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 50° C. and 65° C., depending on primer length. Additional guidelines for determining hybridization parameters are provided in numerous references. Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

The "Clustal V method of alignment" corresponds to the alignment method labeled Clustal V (described by Higgins and Sharp, *CABIOS.* 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Tropical Rust Resistance

Tropical rust resistance is a fungal disease of maize caused by the pathogen *Physopella zeae*. The identification of molecular markers and alleles associated with tropical rust resistance allows selection for resistance based solely on the genetic composition of the progeny. Methods for identifying and selecting maize plants with enhanced resistance to tropical rust through the evaluation of genetic composition (as assessed using molecular markers and their alleles) are presented herein.

Genetic Mapping

It has been recognized for quite some time that specific genetic loci correlating with particular phenotypes, such as resistance to tropical rust, can be mapped in an organism's genome. The plant breeder can advantageously use molecular markers to identify desired individuals by identifying marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a quantitative trait such as resistance to tropical rust. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods that can be used to detect loci of interest are: 1) Population-based association analysis and 2) Pedigree-based association analysis (or traditional linkage mapping). In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to the those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie the pedigree-based association analyses (also referred to as traditional linkage analysis); however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Figure 3:
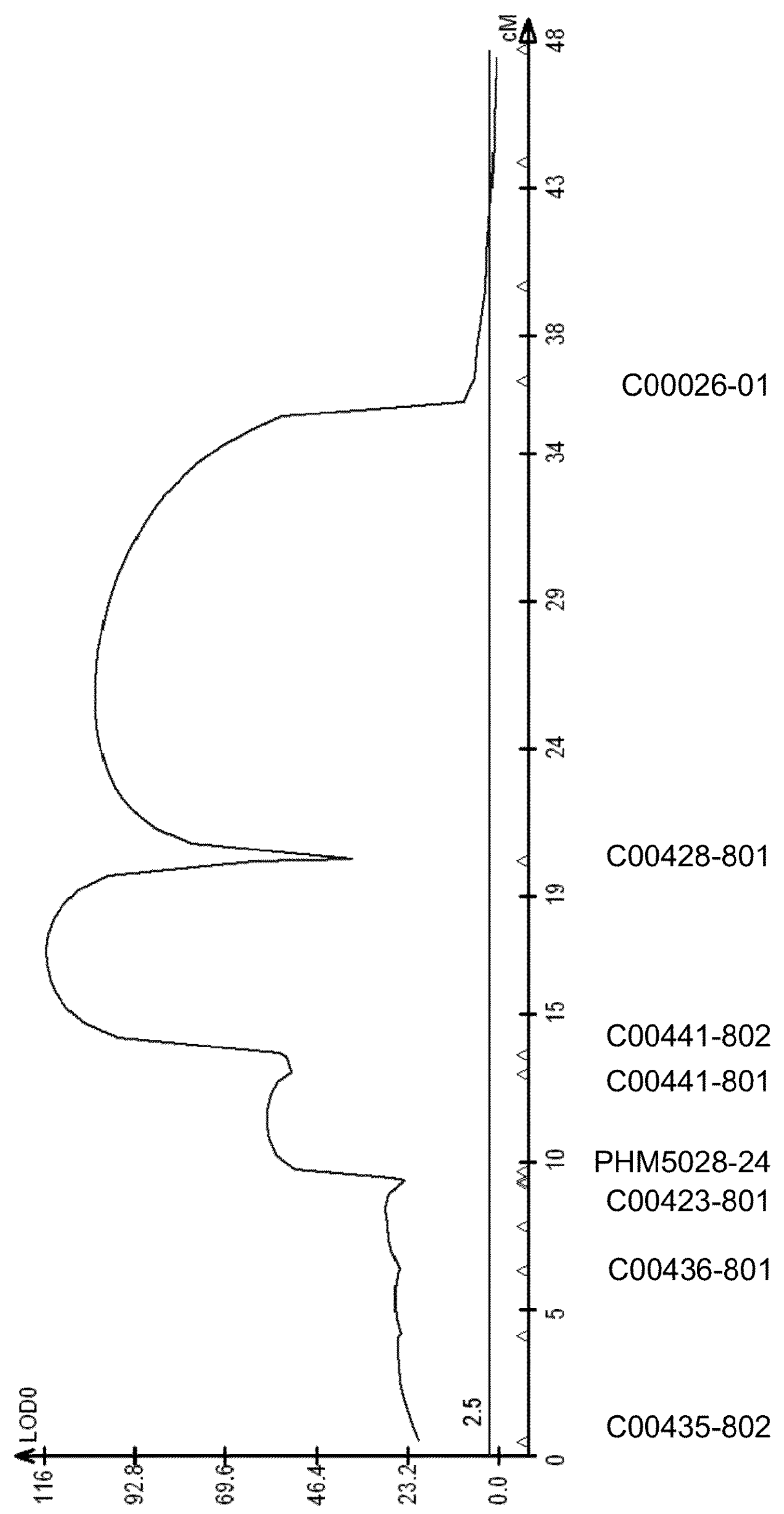

The present invention provides molecular marker loci that demonstrate co-segregation with resistance to tropical rust as determined by traditional linkage analysis (FIG. 3). Detection of these marker loci or additional linked marker loci can be used in marker assisted maize breeding programs to produce plants with enhanced resistance to tropical rust or to eliminate plants with an unfavorable tropical rust phenotype from breeding programs or planting.

Markers Associated with Resistance to Tropical Rust

Markers associated with resistance to tropical rust are identified herein, as are marker alleles associated with either increased (enhanced) or decreased resistance to tropical rust. The methods involve detecting the presence of one or more marker alleles associated with the enhanced resistance in a maize plant or germplasm. The maize plant can be a hybrid or an inbred.

The marker locus can be selected from any of the marker loci provided herein, including but not limited to the SNP production markers PHM1192-26-U, PHM1192-4-U, C00435-802-U, C00436-801-U, PHM187-7-U, C00423-801-U, PHM5028-24-U, PHM13818-15-U, PHM15721-39-U, PHM15721-180-U, C00441-801-U, C00441-802-U, PHM4370-19-U, PHM731-107-U, C00071-01-U, PHM8249-21-U, C00428-801-U, PHM18427-13-U, PHM9535-10-U, PHM9535-6-U, PHM9535-7-U, and PHM4003-13-U; the PHM markers PHM15590, PHM13818, PHM1192, PHM187, PHM5028, PHM4370, PHM731, and PHM15721; Sub2e, Sub9d, Sub19c, Sub23m, C06621-1-K2, and C06621-1-K4, as well as any other marker linked to these markers.

Physical Map Location of the Interval Comprising the Tropical Rust Resistance Gene The genetic elements or genes located on a contiguous linear span of genomic DNA on a single chromosome are physically linked.

The present invention provides molecular marker loci on an area of chromosome 10 defined by and including PHM15590 and PHM15721, thereby delineating a region comprising a gene that confers resistance to tropical rust. PHM15590 is located on BAC c0497L12, and PHM15721 is located on b0191E02. Any polynucleotide that can hybridize or assemble to the contiguous DNA between and including SEQ ID NO:89 (the reference sequence for PHM15590), or a nucleotide sequence that is 95% identical to SEQ ID NO:89 based on the Clustal V method of alignment, and SEQ ID NO:96 (the reference sequence for PHM15721 or a nucleotide sequence that is 95% identical to SEQ ID NO:96 based on the Clustal V method of alignment, and that is associated with tropical rust resistance can be used as a marker for tropical rust. This physical region encompasses marker loci that are shown herein to be associated with the tropical rust resistance trait.

FIG. 1 shows the physical map arrangement of the sequenced B73 BACs that make up the contiguous stretch of DNA between and including BAC c0497L12 and BAC c0352E09. The gaps (represented by open spaces) are not gaps in the contiguous stretch of DNA per se but are areas where genome sequencing information is incomplete.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the tropical rust resistance phenotype, it is important to note that the marker locus is not necessarily part of a gene or QTL locus responsible for the expression of the tropical rust resistance phenotype. For example, it is not a requirement that the marker polynucleotide sequence be part of a gene that imparts tropical rust resistance (for example, be part of the gene open reading frame). The association between a specific marker allele with either a favorable or unfavorable tropical rust resistance phenotype is due to the original "coupling" linkage phase between the marker allele and the founder allele in the ancestral maize line. Eventually, with repeated recombination, crossing over events between the marker and the genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

Markers provided herein can be used to predict the state of the tropical rust resistance trait in a maize plant. This includes any marker within 20, 10, 9, 8, 7, 6, 5, 4, 3, 2, 1, 0.9, 0.8, 0.7, 0.6, 0.5, 0.4, 0.3, 0.2, or 0.1 cM of any of the SNP production markers PHM1192-26-U, PHM1192-4-U, C00435-802-U, C00436-801-U, PHM187-7-U, C00423-801-U, PHM5028-24-U, PHM13818-15-U, PHM15721-39-U, PHM15721-180-U, C00441-801-U, C00441-802-U, PHM4370-19-U, PHM731-107-U, C00071-01-U, PHM8249-21-U, C00428-801-U, PHM18427-13-U, PHM9535-10-U, PHM9535-6-U, PHM9535-7-U, and PHM4003-13-U; the PHM markers PHM15590, PHM13818, PHM1192, PHM187, PHM5028, PHM4370, PHM731, and PHM15721; and the other markers identified herein, Sub2e, Sub9d, Sub19c, Sub23m, C06621-1-K2, and C06621-1-K4.

Chromosomal Intervals

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as markers for tropical rust resistance.

Chromosomal intervals encompassing markers that co-segregate with tropical rust resistance are provided. These intervals are located on chromosome 10 and may be defined by and include:

(i) PHM15590 and PHM9535;
(ii) PHM15590 and PHM15721;
(iii) C00441 and c00428;
(iv) PHM731 and PHM15721; or
(v) c00071 and PHM731.

Any marker located within any of these intervals can find use as a marker for tropical rust resistance.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 10 marker locus lying within the interval of PHM15590 and PHM9535, for example, and another chromosome 10 marker locus in close proximity is greater than ⅓ (Ardlie et al., Nature Reviews Genetics 3:299-309 (2002)), the loci are in linkage disequilibrium with one another.

Marker Alleles and Haplotypic Combinations

A marker of the invention can also be a combination of alleles at one or more marker loci (i.e. a haplotype). The alleles described below could be used alone or in combination to identify and select maize plants with enhanced tropical rust resistance.

Favorable alleles associated with enhanced tropical rust resistance have been identified herein. One such allele is a "T" deletion at position 16 of PHMTR (SEQ ID NO:155). FIG. 7 shows a part of the reference sequence (top) obtained by the genotyping of maize lines resistant and susceptible to tropical rust using PCR primers (SEQ ID NO: 133 and 134) designed for clone ID Ct9050c064G11c (Table 9). SEQ ID NOs: 137-142 represent amplicons obtained from resistant lines, and SEQ ID NOs: 143-154 represent amplicons obtained from susceptible lines. The area highlighted in grey represents a 21 bp-region of the reference sequence (referred to as PHMTR; SEQ ID NO:155). Maize lines having a T-deletion at by 16 of PHMTR (indicated by the arrow) all showed enhanced resistance to tropical rust. Maize lines having an intact PHMTR region all showed sensitivity to tropical rust.

Tables 7 and 8 also show chromosome 10 markers that have been successfully used in combination to convert susceptible inbreds into resistant inbreds using PHS6Y as the source. The alleles possessed by PHS6Y at each of the markers can be used in combination (as a haplotype) to identify and select plants with enhanced resistance to tropical rust.

While a haplotype associated with enhanced resistant to tropical rust may comprise any of the favorable alleles described herein (including the "T" deletion at position 16 of PHMTR and any of the marker alleles possessed by the resistant line PHS6Y in Tables 7 and 8), the "GAG" haplotype at positions 337-339 of reference sequence SEQ ID NO:167 was shown to be associated with enhanced resistance to tropical rust and can be used in a marker assisted selection program to select for maize plants with enhanced resistance to tropical rust.

The skilled artisan would expect that there might be additional polymorphic sites at marker loci in and around the chromosome 10 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, a series of flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 by or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. Pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems), KASPar assays by Kbioscience, and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with enhanced resistance to tropical rust, but the allele 'T' might also occur in the maize breeding population being utilized for recurrent parents. In this case, a haplotype, e.g. a series of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the primers listed in Table 2 can readily be used as FLP markers to select for the gene locus or QTL on chromosome 10 controlling resistance to tropical rust, owing to the presence of insertions/deletion polymorphisms. These primers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with tropical rust resistance. Such markers are presumed to map near a gene or genes that give the plant its tropical rust resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny.

The markers and intervals presented herein find use in MAS to select plants that demonstrate enhanced resistance to tropical rust.

Methods for selection can involve detecting the presence (or absence) of either an identified marker allele or an unknown marker allele that is linked to and associated with an identified marker allele in a maize plant or germplasm and then selecting the maize plant or germplasm based on the allele detected. Favorable alleles identified herein that could be detected in MAS include: the "T" deletion at position 16 of PHMTR and any of the marker alleles possessed by PHS6Y in Tables 7 and 8. In addition, favorable haplotypes, such as the "GAG" haplotype at positions 337-339 of reference sequence SEQ ID NO:167, can also be used in MAS to introduce enhanced resistance to tropical rust into susceptible maize lines or varieties.

Usefulness of MAS for Enhancing Resistance to Tropical Rust in Maize

Maize plant breeders desire combinations of desired genetic loci, such as those marker alleles associated with enhanced resistance to tropical rust, with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to resistance to tropical rust loci, provide an effective method for selecting varieties with enhanced resistance to tropical rust in breeding programs. For example, one advantage of marker-assisted selection over field evaluations for the selection of plants that have enhanced resistance to tropical rust is that MAS can be done at any time of year, regardless of the growing season. Moreover, environmental effects are largely irrelevant to marker-assisted selection.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising enhanced resistance to tropical rust marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because plants may be otherwise undesirable, e.g., due to low yield, low fecundity, or the like. In contrast, strains which are the result of intensive breeding programs may have excellent yield, fecundity or the like, merely being deficient in one desired trait such as resistance to tropical rust.

MAS can increase the efficiency of an introgression or backcrossing effort aimed at introducing enhanced resistance to tropical rust into a desired (typically high yielding) background. In marker assisted backcrossing of specific markers from a donor source, e.g., to an elite or exotic genetic background, one selects among backcross progeny for the donor trait and then uses repeated backcrossing to the elite or exotic line to reconstitute as much of the elite/exotic background's genome as possible.

Multiple Stages Cluster Methodology

A multiple stages cluster methodology can be used to direct primer design into non-random variation. This method uses phylogenetic trees and a sequential alignment process to identify unique regions containing allelic variations exclusive to lines with a desired trait. If any given sequence in a BAC collection contains a variation in DNA to be related to a trait, this variation can be hidden/confounded by other independent and random variations within the same BAC, therefore a single alignment may not be effective in detecting the targeted variation(s). The first stage of this process involves an alignment of raw sequences with an open:extension cost ratio greater than 10. The second stage consists of trimming the tails (noise) and realigning the original sequence, whose cluster will already indicate the BAC potential for bearing a region of interest. Subsequent stages consist of upstream or downstream trimming of random allelic variation, i.e., alleles inside the sequence that showed diversity across any phenotype. UPGMA (Unweighted Pair Group Method with Arithmetic Mean) can then be applied to the resulting alignment until a phenogram identifies a unique cluster exclusive to lines having a desired trait or phenotype. The final cluster can then be used to identify the specific variation that will be used for primer design to generate a trait specific marker.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Phenotypic Assessment of Enhanced Resistance to Tropical and Southern Rust

Maize plants were inoculated in the field with *Physopella zeae* to promote symptoms of tropical rust. Three inoculations were done starting at the V10 stage (each inoculation with ~500,000 spores per ml to a total volume of 200 liters per hectare).

Maize plants were evaluated for enhanced resistance to southern rust (pathogen *Puccinia polysora*) based on natural infection conditions in a field located in Itumbiara, Brazil Tropical rust develops from the top of the plant to the bottom of the plant, while southern rust moves from the bottom of the plant to the top. Thus, in the same plant, it is possible to observe symptoms of both tropical and southern rust diseases.

Two systems were used to score the plants in the field at the R2 stage (around 20 days after pollination time). The first system is on a 1 to 9 scale, where 1=most susceptible and 9=most resistant, while the second system corresponds to the Modified International Standard Scale for Rust (Table 4).

TABLE 4

Scoring Scales for Tropical and Southern Rust

| International Symbol | PiONEER Scale | Description of the host: Parasite interaction |
|---|---|---|
| Oi | 9 | Immune - No signs of infection |
| Oc | 8 | Highly resistant, minute chlorotic flecks |
| On | 7 | Highly resistant, minute necrotic flecks |
| 1 | 6 | Resistant, small pustules with necrotic surrounding tissue |
| 2 | 5 | Mod. Resistant, medium size pustules with necrotic sorrounding tissue |
| 3 | 4 | Mod. Susceptible, medium size pustules with chlorotic surrounding tissue |
| 4 | 2 | Susceptible. Large pustules with little or no chlorosis |
| X | Most Severe score observed | Mesotheric reaction. Mixed reaction types on one leaf |

Example 2

Development of PHS6Y Inbred Population

PHS6Y was developed using a pedigree selection scheme at the Itumbiara Research Center in Brazil. Individual ears were selected in the F2 generation from a cross between PH7W3 and CML339. CML339 (Makumbi et al. Combining Ability and Heterosis in Tropical Maize Inbreds under Stress and Optimal Conditions. The ASA-CSSA-SSSA International Annual Meetings (Nov. 6-10, 2005), Salt Lake City, Utah. 2005) is a line with enhanced resistance to tropical rust that was obtained from the International Maize and Wheat Improvement center (CIMMYT). Each selected F2 ear was planted as an F3 row in the following generation. Three ears from each selected F3 row were then planted in the next generation, and the best F4 row was selected and the seed designated as PHS6Y inbred seed. All selections were performed based on the tropical rust resistance phenotype.

Example 3

Figure 2:
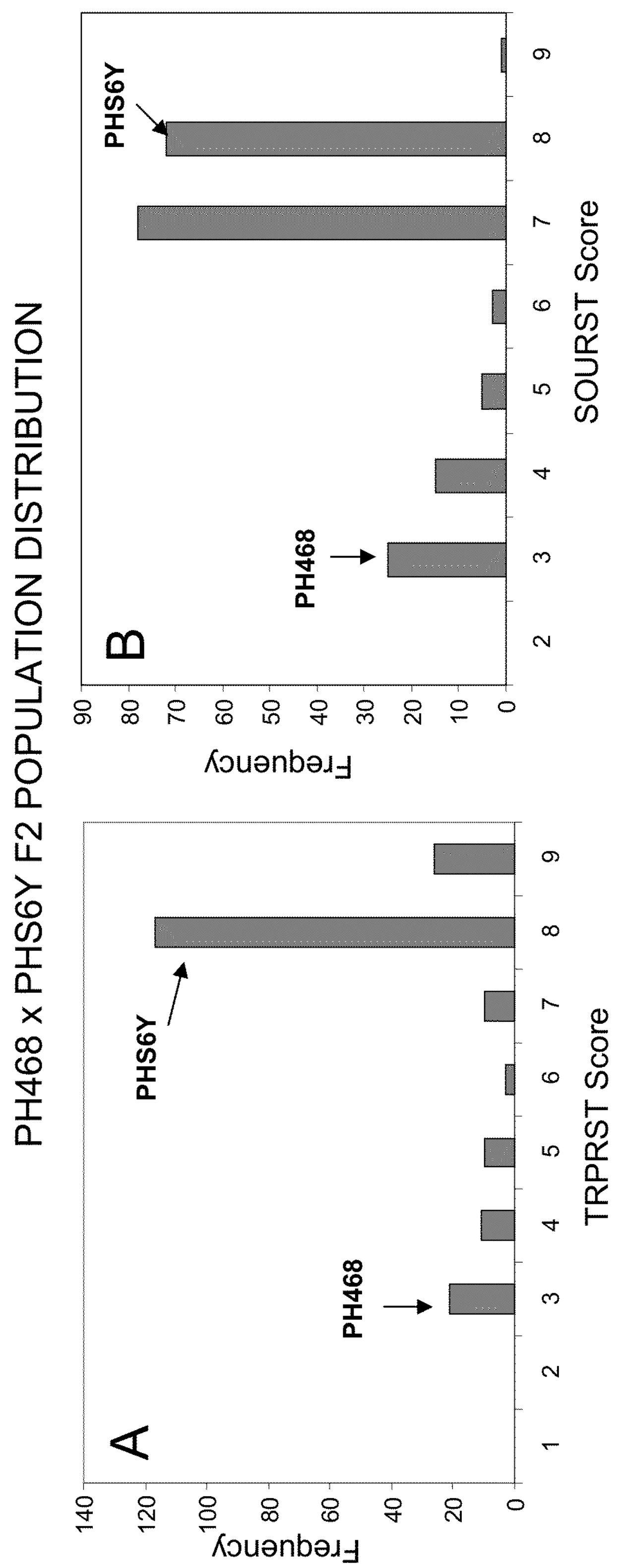

Segregation for Tropical Rust Resistance Indicates that a Single Dominant Gene is Responsible for Conferring Tropical Rust Resistance An F2 population was developed from a cross between PH468, an inbred susceptible to tropical rust, and PHS6Y, the inbred identified in EXAMPLE 2. Frequency distributions demonstrating the tropical and southern rust scores for individuals in the PH468×PHS6Y F2 population are shown in FIGS. 2A and 2B, respectively. Each distribution indicates a segregation ratio of 3 resistant (scores ≥5 on the 1-9 scale): 1 susceptible (scores <5 on the 1-9 scale) for tropical rust (FIG. 2A) and for southern rust (FIG. 2B).

Table 5 shows a Chi-square test which provides evidence for the presence of a single dominant gene that confers resistance to tropical rust, wherein the favorable genotype is present in the PHS6Y inbred. Results also show that a single dominant gene confers resistance to southern rust. However, based on genetic recombination frequencies between tropical and southern resistance in two F2 populations in which PHS6Y is a parent, the genes that confer resistance appear to be different for tropical and southern rust (Table 6).

TABLE 5

| Chi-square Test Results for PH468 × PHS6Y F2 Population Population PH468/PHS6Y | | | | |
|---|---|---|---|---|
| | <5 | ≥5 | p-value | CHI-Square |
| | Tropical rust score # Plants | | | |
| Observed | 305 | 84 | 0.128 | 2.321 |
| Expected | 292 | 97 | | |
| | Southern rust score # Plants | | | |
| Observed | 298 | 91 | 0.482 | 0.494 |
| Expected | 292 | 97 | | |

Table 6 shows the genetic recombination frequencies between tropical and southern resistance in two F2 populations with PHS6Y. Control is another F2 population where both tropical and southern rust traits are also segregating but in an independent manner.

TABLE 6

| Genetic Recombination Between Tropical and Southern Resistance in Two F2 Populations with PHS6Y as a Parent | | | |
|---|---|---|---|
| F2 POPULATION | # Recomb | Total # Pls | % Recomb |
| 468/S6Y | 13 | 389 | 3 |
| 467/S6Y | 18 | 341 | 5 |
| Control (7513/26N) | 126 | 342 | 37 |

468 = PH468;
S6Y = PHS6Y;
467 = PH467

Example 4

Composite Interval Mapping

A composite interval mapping approach that combines interval mapping with linear regression was undertaken to identify maize chromosomal intervals and markers associated with resistance to tropical rust. In an interval mapping approach (Lander and Botstein, Genetics 121:185-199 (1989)), each of many positions along the genetic map (say at 1 cM intervals) is tested for the likelihood that a gene or QTL controlling a trait of interest is located at that position. The genotype/phenotype data are used to calculate for each test position a LOD score (log of likelihood ratio). When the LOD score exceeds a threshold value (herein the threshold value is 2.5), there is significant evidence for the location of a gene or QTL at that position on the genetic map (which will fall between two particular marker loci).

Windows QTL Cartographer (the most up-to-date version of this software was used at the date of QTL mapping) was used to perform the composite interval mapping. LOD scores (logarithm of the odds ratio) were estimated across the genome according to standard QTL mapping procedures.

Results from composite interval mapping for resistance to tropical rust using the PH468×PHS6Y F2 population are shown in FIG. 3. The composite interval mapping analysis detected a large effect QTL on chromosome 10 (FIG. 3) located between markers C00441-801 and C00428-801. The linkage map used for composite interval mapping was an internally-derived proprietary genetic map (identified herein as "PHB") for which the genetic distances correspond to a single meiosis recombination fraction. Marker positions on the x-axis correspond to the PHB genetic map. The y-axis represents the LOD score.

Example 5

Backcrossing of the Tropical Rust Resistance Locus from PHS6Y into Susceptible Inbred Lines The tropical rust resistant inbred line PHS6Y was elected as the donor parent for the backcrossing program. This inbred line carries a favorable allele within the segment of Chromosome 10 harboring the tropical rust gene. In the initial backcrossing program, four inbred lines (PH9VF, PHDGA, PH467 and PH0TJ) were elected to be converted with the tropical rust resistance locus from PHS6Y.

Each inbred line (PH9VF, PHDGA, PH467 and PH0TJ) was crossed to PHS6Y. After obtaining F1 seed from each cross, five subsequent backcrosses were performed in which the susceptible parent was used as the recurrent parent. Two generations a year were evaluated to accelerate the process, one in North of Brazil at the Balsas Winter Nursery location and the other at Itumbiara Research Center. In the first backcross, only phenotypic selection was done at Itumbiara center. In subsequent backcrosses, marker-assisted selection was performed. The backcrossing process was followed by two generations of selfing to fix the resistant allele in each inbred.

Three to six markers were used in the process of converting each inbred (Table 7). The markers were used in the Backcross 2 (BC2) generation up to the BC4 generation as well as for the identification of homozygous plants carrying the resistance alleles at BC4F2.

Table 7 shows the markers on Chromosome 10 that were used for introgressing the resistance locus from PHS6Y into inbreds PH9VF, PHDGA, PH467, and PH0TJ, and the polymorphisms between each susceptible inbred and PHS6Y.

Other inbreds were converted to have the tropical rust resistance locus from PHS6Y. The conversions were done similarly as described above except more markers were used for the conversion. Table 8 shows the markers on Chromosome 10 that were used for introgressing the resistance locus from PHS6Y into 18 inbreds and the polymorphisms between each susceptible inbred and PHS6Y.

TABLE 7

| Chromosome 10 Markers Used for Conversion of Four Inbreds | | | | | | | |
|---|---|---|---|---|---|---|---|
| | PHB | | | | | | |
| | 4 | 9.7 | 12.6 | 12.6 | 15 | 18.2 | 19.5 |
| INBRED | PHM1192-26 | PHM5028-24 | PHM15721-180 | PHM15721-39 | C00071-01 | PHM731-107 | PHM8249-21 |
| PHS6Y | 1, 1 | 4, 4 | 2, 2 | 6, 6 | 6, 6 | 2, 2 | 2, 2 |
| PH9VF | 1, 1 | 4, 4 | 2, 2 | 5, 5 | 5, 5 | 4, 4 | 2, 2 |

TABLE 7-continued

Chromosome 10 Markers Used for Conversion of Four Inbreds

| | | | | | | | |
|---|---|---|---|---|---|---|---|
| PHDGA | 1, 1 | 2, 2 | 2, 2 | 6, 6 | 5, 5 | 4, 4 | 2, 2 |
| PH467 | 1, 1 | 2, 2 | 2, 2 | | 5, 5 | 2, 2 | 4, 4 |
| PH0TJ | 3, 3 | 2, 2 | 4, 4 | 6, 6 | 6, 6 | 4, 4 | 2, 2 |

| | PHB | | | | |
|---|---|---|---|---|---|
| INBRED | 20.4<br>PHM18427-13 | 24.2<br>PHM9535-10 | 24.2<br>PHM9535-6 | 24.2<br>PHM9535-7 | 25.4<br>PHM4003-13 |
| PHS6Y | 6, 6 | 3, 3 | 1, 1 | 3, 3 | 2, 2 |
| PH9VF | 6, 6 | 4, 4 | 4, 4 | 1, 1 | 2, 2 |
| PHDGA | 6, 6 | 3, 3 | 1, 1 | 3, 3 | 2, 2 |
| PH467 | 5, 5 | 3, 3 | 4, 4 | 1, 1 | 4, 4 |
| PH0TJ | 6, 6 | 3, 3 | 1, 1 | 3, 3 | 2, 2 |

1 = “A”,
2 = “C”,
3 = “G”,
4 = “T”,
5 = “I” or insertion,
6 = “D” or deletion

TABLE 8

Chromosome 10 Markers Used for Conversion of Eighteen Inbreds

| | C00071-01 | PHM1192-26 | PHM1192-4 | PHM13818-15 | PHM15721-180 |
|---|---|---|---|---|---|
| PHS6Y | 6, 6 | 1, 1 | 5, 5 | 2, 2 | 2, 2 |
| PH92E | 6, 6 | 1, 1 | 6, 6 | 2, 2 | 4, 4 |
| PH0R8 | 6, 6 | 3, 3 | n/a | n/a | 2, 4 |
| PH0TJ | 6, 6 | 3, 3 | 5, 5 | 2, 2 | 4, 4 |
| PH1BC | 6, 6 | 1, 1 | 6, 6 | 2, 2 | 4, 4 |
| PHS6M | 6, 6 | 3, 3 | 5, 5 | 2, 2 | 2, 2 |
| PHKTE | 6, 6 | 3, 3 | n/a | n/a | 2, 4 |
| PHS7S | 5, 5 | 1, 1 | 5, 5 | 2, 2 | 2, 2 |
| PH9TJ | 5, 5 | 1, 1 | 5, 5 | 2, 2 | 2, 2 |
| PHBNF | 5, 5 | 1, 1 | 5, 5 | 2, 2 | 2, 2 |
| PHD18 | 5, 5 | 1, 1 | 5, 5 | 2, 2 | 2, 4 |
| PHR33 | 6, 6 | 3, 3 | 5, 5 | 2, 2 | 2, 4 |
| PH9VC | 6, 6 | 1, 1 | 6, 6 | 2, 2 | 2, 2 |
| PHKNC | 5, 5 | 1, 1 | n/a | 2, 2 | 2, 2 |
| PH819 | 6, 6 | 1, 1 | 6, 6 | 2, 2 | 2, 2 |
| PHKNF | 6, 6 | 1, 1 | 5, 5 | 2, 2 | 2, 2 |
| PH9V7 | 5, 5 | 1, 1 | 5, 5 | 2, 2 | 2, 2 |
| PHDNV | 5, 5 | 1, 1 | 5, 5 | 4, 4 | 2, 2 |
| PHM3M | 5, 5 | 1, 1 | 5, 5 | 4, 4 | 2, 2 |

| | PHM15721-39 | PHM18427-13 | PHM187-7 | PHM4003-13 | PHM4370-19 |
|---|---|---|---|---|---|
| PHS6Y | 6, 6 | 6, 6 | 1, 1 | 2, 2 | 3, 3 |
| PH92E | n/a | 5, 5 | 1, 1 | 2, 2 | 3, 3 |
| PH0R8 | n/a | 6, 6 | n/a | 2, 2 | 3, 3 |
| PH0TJ | 6, 6 | 6, 6 | 3, 3 | 2, 2 | 3, 3 |
| PH1BC | 6, 6 | 5, 5 | 1, 1 | 2, 2 | 3, 3 |
| PHS6M | n/a | n/a | 3, 3 | 2, 2 | 3, 3 |
| PHKTE | 6, 6 | 6, 6 | 3, 3 | 2, 2 | 3, 3 |
| PHS7S | 5, 5 | 6, 6 | 1, 1 | 2, 2 | 3, 3 |
| PH9TJ | 6, 6 | 6, 6 | 1, 1 | 2, 4 | 3, 3 |
| PHBNF | 6, 6 | 6, 6 | 1, 1 | 2, 2 | 3, 3 |
| PHD18 | 6, 6 | 6, 6 | 1, 1 | 2, 2 | 3, 3 |
| PHR33 | 6, 6 | 6, 6 | 3, 3 | 2, 2 | 3, 3 |
| PH9VC | 5, 5 | 5, 5 | 1, 1 | 2, 2 | 1, 1 |
| PHKNC | 5, 5 | 6, 6 | 1, 1 | 2, 2 | 3, 3 |
| PH819 | 5, 5 | 5, 5 | 1, 1 | 2, 2 | 1, 1 |
| PHKNF | 5, 5 | 6, 6 | 1, 1 | 2, 2 | 3, 3 |
| PH9V7 | 6, 6 | 6, 6 | 1, 1 | n/a | 3, 3 |
| PHDNV | 6, 6 | 6, 6 | 1, 1 | 2, 2 | 3, 3 |
| PHM3M | 6, 6 | 6, 6 | n/a | 4, 4 | 3, 3 |

TABLE 8-continued

Chromosome 10 Markers Used for Conversion of Eighteen Inbreds

| | PHM5028-24 | PHM731-107 | PHM9535-10 | PHM9535-6 | PHM9535-7 |
|---|---|---|---|---|---|
| PHS6Y | 4, 4 | 2, 2 | 3, 3 | 1, 1 | 3, 3 |
| PH92E | 4, 4 | 2, 2 | 3, 3 | 1, 1 | 3, 3 |
| PH0R8 | 2, 2 | 4, 4 | 3, 3 | 1, 1 | 3, 3 |
| PH0TJ | 2, 2 | 4, 4 | 3, 3 | 1, 1 | 3, 3 |
| PH1BC | 4, 4 | n/a | 4, 4 | 4, 4 | n/a |
| PHS6M | 2, 2 | n/a | 3, 3 | 4, 4 | 1, 1 |
| PHKTE | 2, 2 | n/a | 3, 3 | 1, 1 | n/a |
| PHS7S | 4, 4 | n/a | 4, 4 | 4, 4 | 1, 1 |
| PH9TJ | 4, 4 | 2, 2 | 3, 3 | 4, 4 | 3, 3 |
| PHBNF | 4, 4 | 4, 4 | 4, 4 | 4, 4 | 1, 1 |
| PHD18 | 4, 4 | 4, 4 | 3, 3 | 1, 1 | 3, 3 |
| PHR33 | 2, 2 | 4, 4 | 3, 3 | 1, 1 | 3, 3 |
| PH9VC | 2, 2 | 4, 4 | 4, 4 | 1, 1 | 3, 3 |
| PHKNC | 4, 4 | 4, 4 | 3, 3 | 4, 4 | 1, 1 |
| PH819 | 2, 2 | 2, 2 | 4, 4 | 1, 1 | 3, 3 |
| PHKNF | 4, 4 | 4, 4 | 3, 3 | 4, 4 | 1, 1 |
| PH9V7 | 4, 4 | 2, 2 | 3, 3 | 4, 4 | 3, 3 |
| PHDNV | 2, 2 | n/a | 3, 3 | 1, 1 | 3, 3 |
| PHM3M | 4, 4 | n/a | 3, 3 | 4, 4 | n/a |

| | C00435-802-U | C00436-801 | C00423-801 | C00441-801 | C00441-802 | C00428-801 |
|---|---|---|---|---|---|---|
| PHS6Y | 4, 4 | 3, 3 | 4, 4 | 3, 3 | 4, 4 | 1, 1 |
| PH92E | 1, 1 | n/a | 2, 2 | 4, 4 | n/a | 1, 1 |
| PH0R8 | n/a | n/a | n/a | n/a | n/a | 3, 3 |
| PH0TJ | 1, 1 | 1, 1 | 2, 2 | 4, 4 | 2, 2 | 3, 3 |
| PH1BC | 1, 1 | 3, 3 | n/a | 4, 4 | n/a | 1, 1 |
| PHS6M | 1, 1 | 1, 1 | 2, 2 | 4, 4 | 2, 2 | 1, 1 |
| PHKTE | n/a | 1, 1 | n/a | 4, 4 | 2, 2 | 3, 3 |
| PHS7S | 4, 4 | 3, 3 | 4, 4 | 3, 3 | 4, 4 | 3, 3 |
| PH9TJ | 4, 4 | 3, 3 | 2, 2 | 4, 4 | 2, 2 | 1, 1 |
| PHBNF | n/a | n/a | n/a | n/a | n/a | n/a |
| PHD18 | n/a | n/a | n/a | n/a | n/a | n/a |
| PHR33 | 1, 1 | 1, 1 | 2, 2 | 4, 4 | 2, 2 | 3, 3 |
| PH9VC | 1, 1 | 1, 1 | n/a | 4, 4 | n/a | 3, 3 |
| PHKNC | n/a | n/a | n/a | n/a | n/a | n/a |
| PH819 | 1, 1 | 3, 3 | n/a | 4, 4 | n/a | 3, 3 |
| PHKNF | 4, 4 | n/a | 4, 4 | n/a | n/a | 3, 3 |
| PH9V7 | n/a | n/a | n/a | n/a | n/a | n/a |
| PHDNV | 1, 1 | n/a | 2, 2 | 4, 4 | 2, 2 | 1, 1 |
| PHM3M | n/a | 1, 1 | n/a | n/a | n/a | 1, 1 |

1 = "A",
2 = "C",
3 = "G",
4 = "T",
5 = "I" or insertion,
6 = "D" or deletion

Example 6

Hybrid Production with Enhanced Resistance to Tropical Rust

Figure 4:
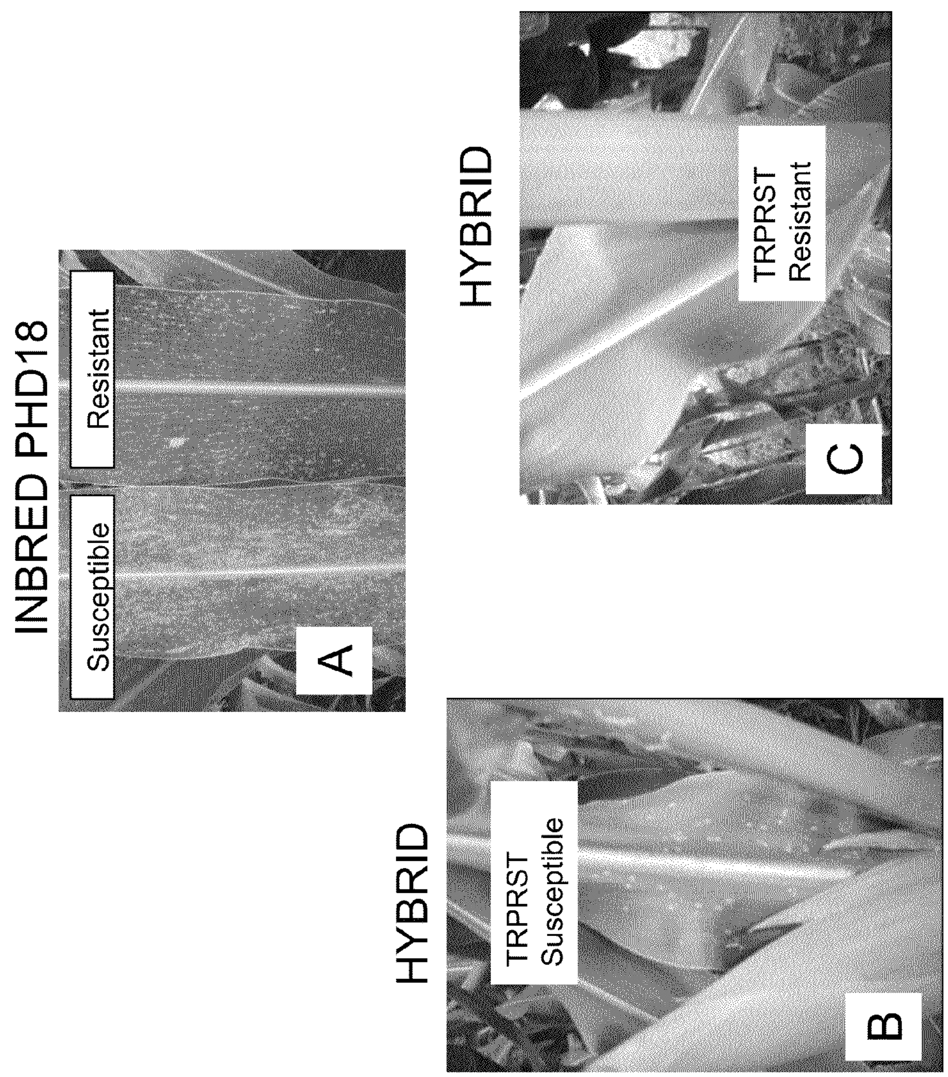
Figure 5:
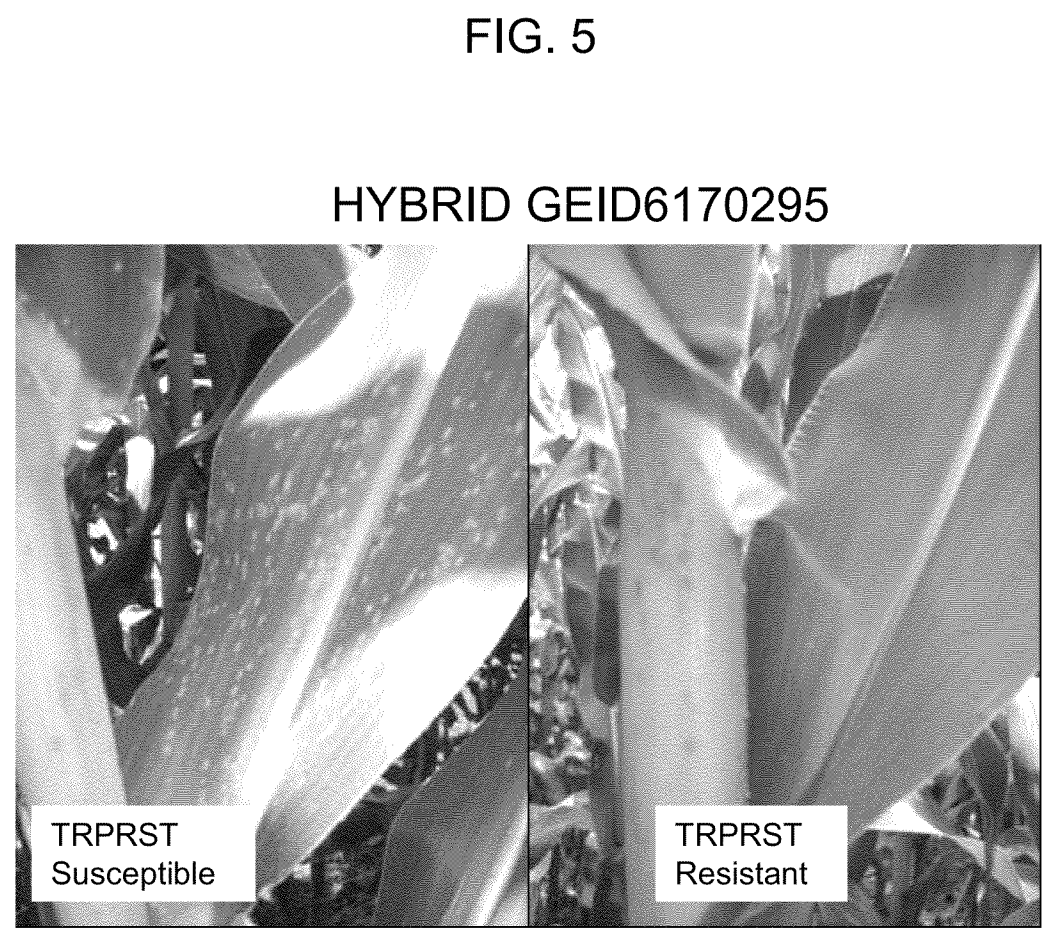

The converted inbreds were used to make hybrids, and the field trial results have shown that the excellent level of resistance seen in the converted inbreds (for example, FIG. 4) is maintained in hybrids made with the conversion inbreds (FIG. 5; e.g. hybrid GEID6170295).

Example 7

Genotyping of Maize Lines for Tropical Rust Resistance and Identification of Polymorphisms Associated with Enhanced Tropical Rust Resistance Genotyping of Maize Lines for Tropical Rust Resistance Resistant and susceptible lines were genotyped by Sanger re-sequencing of genomic targets. The targets were PCR-amplified products from single-copy genomic sections of the tropical rust QTL region mapped on the short arm of chromosome 10.

Figure 6:
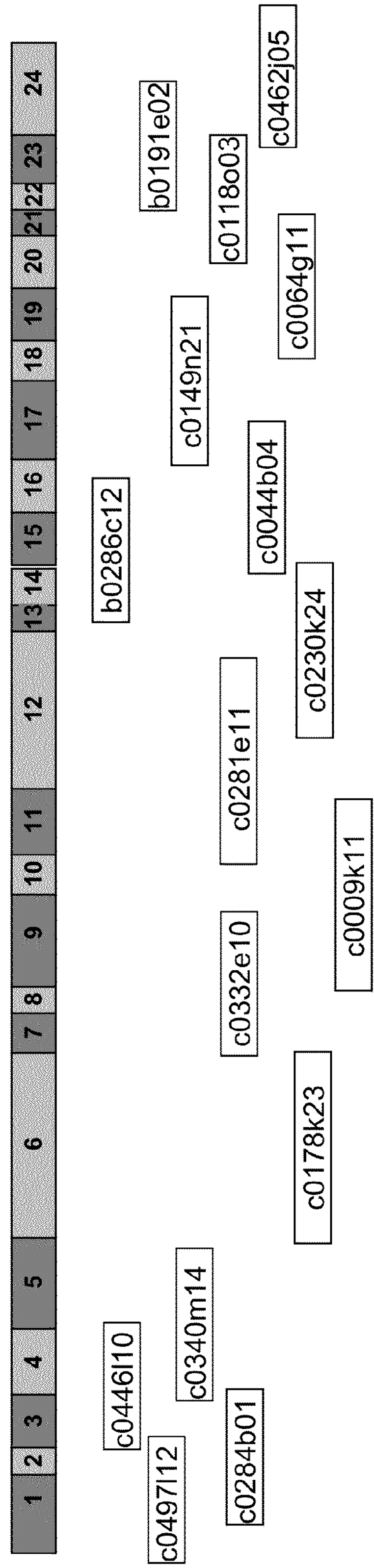
FIG. 6 shows the public BAC clones used as reference for primer design to genotype maize lines that are resistant and susceptible to tropical rust. Internal information regarding BAC overlap was used to further narrow the sequence order of the 2-2.5 Mb region into 24 sub-regions.

Available public genomic sequence was used as reference for primer design. The public sequence corresponds to inbred line B73 and was obtained by a BAC minimum tiling path strategy (available on the Maize Genome Browser, which is publicly available on the internet). The following sequenced BAC clones have been mapped to the region of interest: c0497l12, c0284b01, c0446l10, c0340 m14, c0178k23, c0332e10, c0009k11, c0281e11, c0230k24, b0286c12, c0044b04, c0149n21, c0064g11, c0118o03, b0191e02, c0462j05. While the order and orientation of the BACs in the tiling path has been determined by fingerprinting (Nelson et al, 2005. Whole-Genome Validation of High-Information-Content Fingerprinting. Plant Physiology. 139:27-38), the order and orientation of sequence contigs within each clone has not been fully determined. For this work, internal information on BAC overlap was used to further narrow the sequence order of the 2-2.5 Mb region into 24 sub-regions (FIG. 6).

The sequence includes large portions of highly repetitive DNA, mostly as retrotransposon-like sequences. Multiple-copy sequence tracks were identified and removed from the sequence by masking repeats using Cross-match (http://www.phrap.org). Low copy sequences were further identified and removed by BLAST analysis.

PCR primers were initially designed to amplify 270 to 720-bp amplicons in single-copy tracts spanning the 24 sub-regions in the chromosome 10 target region (Table 9). Primers sets were designed using proprietary tools based on Primer3 (Rozen, S. and Skaletsky, 2000, Primer3 on the WWW for general users and for biologist programmers, Methods Mol Biol. 132:365-386.). Sequencing primers M13R (5-GGAAACAGCTATGACCATG) and M13F (5-TGTAAAACGACGGCCAGT) were added to the L and R primers, respectively, as tails to facilitate sequencing. Quality and uniqueness of PCR assays were validated by performing and analyzing preliminary PCR and sequencing on control DNA samples from lines B73 and Mo17. Maize-oat addition line amplification was used to further validate assays. PCR primers that produced amplified products in multiple addition lines or did not produce an amplified product exclusively in the chromosome 10 maize-oat addition line were discarded.

TABLE 9

PCR primers Designed to Amplify Products in the Chromosome 10 Target Region

| Marker Name | Sub-region | B73 BAC | Clone ID | L primer (no M13 tail) | R primer (no M13 tail) | Size (bp) |
|---|---|---|---|---|---|---|
| Sub2e | 2 | c0497L12 | Ct9050c497L12e | SEQ ID NO: 129 | SEQ ID NO: 130 | 616 |
| Sub19d | 19 | c0064G11 | Ct9050c064G11d | SEQ ID NO: 131 | SEQ ID NO: 132 | 601 |
| Sub19c | 19 | c0064G11 | Ct9050c064G11c | SEQ ID NO: 133 | SEQ ID NO: 134 | 649 |
| Sub23m | 23 | c0462J05 | Ct9050b191E02m | SEQ ID NO: 135 | SEQ ID NO: 136 | 605 |

PCR was performed on 10-30 ng DNA using HotStar Taq Polymerase Master Mix (Qiagen), according to recommendations by the manufacturers with some modifications. The total reaction volume was 10 μl and contained 5U HotStar Taq DNA polymerase, 1.5 mM MgCl2, 200 μM dNTPs and 5 pM of each tailed primer. PCR amplification was performed as follows: 1) 15-minute initial step at 95° C.; 2) 40 cycles of 30 seconds at 95° C., 30 seconds at 60° C., 1 minute at 72° C.; and 3) final extension step of 10 minutes at 72° C. PCR products were confirmed by gel electrophoresis. One fifth (2 μl) of the PCR reaction was diluted in 17 μl of sterile distilled water and cleaned up with 0.5 to 0.75 μl ExoSAP-IT (USB Corporation), incubating at 37° C. for 25 min then 80° C. for 25 min.

Bidirectional cycle sequencing of PCR amplicons was performed using Big Dye Terminator cycle sequencing protocols and capillary sequencing in Applied Biosystems 3730 XL DNA analyzers. 3-5 μl of the cleaned-up DNA was sequenced using M13F and M13R oligonucleotides and the BigDye Prism sequencing kit (ABI; version 3.1), according to manufacturer conditions. After cycle sequencing, reaction products were cleaned up by ethanol precipitation and processed on ABI3730xl automated sequencers (ABI), according to standard protocols.

Sequences were assembled using internal tools based on the Phrap, Phred software, (Ewing et al, 1998, Basecalling of automated sequencer traces using phred. I. Accuracy assessment. Genome Research. 8:175-185; Ewing and Green, 1998, Basecalling of automated sequencer traces using phred. II. Error probabilities. Genome Research. 8:186-194). Polymorphisms (single nucleotide and insertion-deletions) were identified and tagged using the Consed sequence viewer (Gordon, 2003, Viewing and Editing Assembled Sequences Using Consed, in Current Protocols in Bioinformatics, A. D. Baxevanis and D. B. Davison (eds), New York: John Wiley & Co., 2004, 11.2.1-11.2.43). Generated SNP tables, assembly sets and consensus sequences were used to select appropriate polymorphisms for marker development.

Identification of Polymorphisms Associated with Enhanced Resistance to Tropical Rust DNA fragments bearing a high level of internal diversity are more likely to contain genes of interest. However, designing primers in these regions can be difficult because primer design applications have a tendency to select areas of random variation for primer design. A multiple stages cluster methodology was tested in order to direct primer design into non-random variation. This method uses phylogenetic trees and a sequential alignment process to identify unique regions containing allelic variations exclusive to lines with enhanced resistance to tropical rust. The first stage of this process involves an alignment of raw sequences with an open:extension cost ratio greater than 10. The second stage consists of trimming the tails (noise). Subsequent stages consist of trimming random allelic variation, i.e., alleles inside the sequence that showed diversity across any phenotype. UPGMA (Unweighted Pair Group Method with Arithmetic Mean) is then applied to the resulting alignment until a phenogram identifies a unique cluster exclusive to resistant lines.

One primer pair (SEQ ID NO:133 and SEQ ID NO:134) produced an amplicon with the reference sequence (SEQ ID NO:155) that is referred to herein as PHMTR. All lines that showed resistance to tropical rust contained a T-deletion of by 16 of PHMTR (the sequence of the PHMTR-T region is SEQ ID NO:156) while all maize lines susceptible to tropical rust contained an intact PHMTR region (SEQ ID NO: 155).

FIG. 7 shows a part of the reference sequence (top) obtained by the genotyping of maize lines resistant and susceptible to tropical rust using PCR primers (SEQ ID NO: 133 and 134) designed for clone ID Ct9050c064G11c (Table 9). SEQ ID NOs:137-142 represent amplicons obtained from resistant lines, while SEQ ID NOs:143-154 represent amplicons obtained from susceptible lines. The area highlighted in grey represents a 21 bp-region of the reference sequence (SEQ ID NO:155).

Amplicon sequences were also obtained using primers SEQ ID NO:135 and SEQ ID NO:136 (SEQ ID NO:167 is the reference sequence for this region) and eight independent clusters. Table 10 shows 21 lines evaluated for the cluster analysis. A GAG haplotype (at positions 337-339 of reference sequence SEQ ID NO:167; see FIG. 8) was found to be unique to all lines with enhanced resistance to tropical rust (Table 10 and FIG. 8). Two new presence/absence markers were developed to assay this haplotype, C06621-1-K2 and C06621-1-K4 (Table 3; SEQ ID NOs: 157-164), using the KASPar assay techniques described on the kbioscience website. C06621-1-K2 and C06621-1-K4 are X/P type markers, where X indicates absence and P indicates presence. The P marker detects the GAG polymorphism and the X marker detects ADH, an internal control gene, which is used to show that the reaction worked. Eighteen lines were evaluated with the C06621-1-K2 and C06621-1-K4 markers. All fit the expectation for both markers (except one sample that had missing data) given their cluster analysis.

TABLE 10

Exclusive Haplotype in Lines with Enhanced Tropical Rust Resistance

| Group | Line | Haplotype | Trait |
|---|---|---|---|
| A | PHS6Y | GAG | Tropical and Southern rust |
| A | PH1FT71 | GAG | Tropical and Southern rust |
| A | PH1JG22 | GAG | Tropical and Southern rust |
| A | PH1G3H1 | GAG | Tropical and Southern rust |
| A | PH1JG01 | GAG | Tropical and Southern rust |
| B | PH9VF | ACA | None |
| C | A63 | ACG | None |
| C | PH9PR | ACG | None |
| C | PH7WC | ACG | None |
| C | PH48F | ACG | None |
| C | PHDGA | ACG | None |
| C | A63-1 | ACG | None |
| C | PH7W3 | ACG | None |
| C | PH0TJ | ACG | None |
| D | PHBNA | GCG | None |
| D | Mo17 | GCG | None |
| D | PH467 | GCG | None |
| D | PH147G5 | GCG | Common rust |
| D | PHP3P1 | GCG | Common rust |
| D | PH1AGK1 | GCG | Common rust |
| D | PHY7M2 | GCG | Common rust |

The multiple stages cluster methodology proved to be an efficient method to identify unique regions containing allelic variations exclusive to lines with enhanced resistance to tropical rust, and this methodology can be applied to any trait of interest.

Example 8

Markers and/or Haplotypes for Use in Marker Assisted Selection of Maize Plants with Enhanced Resistance to Tropical Rust A set of common markers can be used to aid in the identification of other markers that can be used to select for maize plants with enhanced resistance to tropical rust. Table 11 shows markers identified herein that define the interval comprising a gene that confers resistance to tropical rust. Markers are in physical map order (as depicted in FIG. 1). The positions of the markers on the PHB internally derived map (based on single meiosis) and on the IBM2 neighbors genetic map (high resolution B73/Mo17 genetic map) are also shown.

TABLE 11

Molecular Marker Positions on the PHB map and the IBM2 Neighbors map

| Marker Locus | PHB map position (cM) | IBM2 neighbors |
|---|---|---|
| PHM15590 | 11.7 | na |
| C00441-801 | 13.0 | na |
| C00441-802 | 13.6 | na |
| PHM13818-15 | 10.8 | na |
| PHM1192-26 | 4.1 | na |
| PHM1192-4 | 4.1 | na |
| PHM187-7 | 9.3 | na |
| C00435-802 | 6.3 | na |
| C00436-801 | 7.8 | na |
| PHM5028-24 | 9.7 | na |
| C00423-801 | 9.4 | na |
| PHM4370-19 | 15.0 | na |
| C00071-01 | 18.2 | na |
| C00428-801 | 20.2 | na |
| PHM731-107 | 18.2 | 19.1 |
| PHM15721-39 | 12.6 | na |
| PHM15721-180 | 12.6 | na |
| PHM8249-21 | 19.5 | na |
| PHM18427-13 | 20.4 | na |
| PHM4003-13 | 25.4 | na |
| PHM9535-10 | 24.2 | 29.6 |
| PHM9535-6 | 24.2 | 29.6 |
| PHM9535-7 | 24.2 | 29.6 |

na = not available

Closely linked markers flanking the locus of interest that have alleles in linkage disequilibrium with a resistance allele at that locus may be effectively used to select for progeny plants with enhanced resistance to tropical rust. Thus, the markers described herein, such as those listed in Table 11, as well as other markers genetically or physically mapped to the same chromosomal segment, may be used to select for maize plants with enhanced resistance to tropical rust. Typically, a set of these markers will be used, (e.g., 2 or more, 3 or more, 4 or more, 5 or more) in the flanking region above the gene and a similar set in the flanking region below the gene. Optionally, a marker within the actual gene and/or locus may also be used. The parents and their progeny are screened for these sets of markers, and the markers that are polymorphic between the two parents are used for selection. The most proximal polymorphic markers to the gene or locus are used to select for the gene or locus, and the more distal polymorphic markers are used to select against the gene or locus. In an introgression program, this allows for selection of the gene or locus genotype at the more proximal polymorphic markers and selection for the recurrent parent genotype at the more distal polymorphic markers.

A haplotype, or a combination of alleles, can also be used to select for plants in a breeding program. Haplotypes can be more informative than single polymorphisms and can be more descriptive of any particular genotype. Once a unique haplotype has been assigned to a donor chromosomal region, such as a haplotype for PHS6Y in the short arm of chromosome 10, that haplotype can be used in that population or any subset thereof to determine whether an individual has a particular gene. Using automated high throughput marker detection platforms known to those of ordinary skill in the art makes this process highly efficient and effective. The marker alleles disclosed herein can be used alone or in combination to select for plants with enhanced resistance to tropical rust through the use of marker assisted selection.

What is claimed:

1. A method of selecting a maize plant with enhanced resistance to tropical rust comprising:
- a. detecting in the maize plant a first marker allele that is linked to and associated with:
  - i. the sequence set forth in SEQ ID NO:156; or
  - ii. a "GAG" haplotype at positions 337-339 of reference sequence SEQ ID NO:167; and
- b. selecting said maize plant that has the first marker allele.

2. The method of claim 1, wherein the first marker allele is linked to the sequence set forth in SEQ ID NO:156 or the "GAG" haplotype at positions 337-339 of reference sequence SEQ ID NO:167 by 20 cM on a single meiosis map.

3. The method of claim 1, wherein the first marker allele is linked to the sequence set forth in SEQ ID NO:156 or the "GAG" haplotype at positions 337-339 of reference sequence SEQ ID NO:167 by 2 cM on a single meiosis map.

4. A method of selecting a maize plant with enhanced resistance to tropical rust comprising:
- a. detecting in the maize plant
  - i. the sequence set forth in SEQ ID NO:156 or
  - ii. a "GAG" haplotype at positions 337-339 of reference sequence SEQ ID NO:167; and
- b. selecting said maize plant that has the sequence set forth in SEQ ID NO:156 or the "GAG" haplotype at positions 337-339 of reference sequence SEQ ID NO:167.

5. A method of selecting a maize plant that displays enhanced resistance to tropical rust, the method comprising:
- a. obtaining a first maize plant that comprises within its genome:
  - i. the sequence set forth in SEQ ID NO:156; or
  - ii. a haplotype comprising a "GAG" at positions 337-339 of reference sequence SEQ ID NO:167;
- b. crossing said first maize plant to a second maize plant;
- c. evaluating progeny plants for the sequence set forth in SEQ ID NO:156 or the haplotype comprising a "GAG" at positions 337-339 of reference sequence SEQ ID NO:167; and
- d. selecting progeny plants that possess the sequence set forth in SEQ ID NO:156 or the haplotype comprising a "GAG" at positions 337-339 of reference sequence SEQ ID NO:167.

* * * * *